(12) United States Patent
Massey et al.

(10) Patent No.: US 6,268,507 B1
(45) Date of Patent: Jul. 31, 2001

(54) HYDANTOIN DERIVATIVES

(75) Inventors: Steven Marc Massey; James Allen Monn, both of Indianapolis; Matthew John Valli, Zionsville, all of IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/637,143

(22) Filed: Aug. 11, 2000

Related U.S. Application Data

(62) Division of application No. 09/322,651, filed on May 28, 1999, now Pat. No. 6,160,009, which is a division of application No. 09/078,337, filed on May 13, 1998, now Pat. No. 5,958,960.
(60) Provisional application No. 60/047,011, filed on May 14, 1997.

(51) Int. Cl.[7] ............................ C07D 487/10; C07F 9/28; A61K 31/415
(52) U.S. Cl. .................. 548/301.4; 548/119; 514/385
(58) Field of Search ................... 548/301.4, 119; 514/385

(56) References Cited

U.S. PATENT DOCUMENTS

| | | | |
|---|---|---|---|
| 5,661,184 | 8/1997 | Helton et al. | 514/574 |
| 5,726,320 | 3/1998 | Robey | 548/301 |
| 5,750,566 | 5/1998 | Monn et al. | 514/510 |
| 5,882,671 | 3/1999 | Helton et al. | 424/456 |
| 5,912,248 | 6/1999 | Fernandez et al. | 514/256 |
| 5,916,920 | 6/1999 | Fernandez et al. | 514/561 |
| 5,958,960 | * 9/1999 | Massey et al. | 514/393 |

FOREIGN PATENT DOCUMENTS

| | | |
|---|---|---|
| 0696577 A1 | 2/1996 | (EP) . |
| 0751117 A1 | 1/1997 | (EP) . |
| 0774454 A1 | 5/1997 | (EP) . |
| 96/04900 | 2/1996 | (WO) . |
| 96/04901 | 2/1996 | (WO) . |

OTHER PUBLICATIONS

James A. Monn et. al., J. Med. Chem., 1997, 40, 528–537.
K. Shimamoto and Y. Ohfune, J. Med. Chem., 1996, 39, 407–423.
Yasufumi Ohfune et al., Bioorganic and Medicinal Chemistry Letters, vol. 3, No. 1, 15–18, 1993.
Haruhiko Shinozaki, Eur. Neurol 1994; 34 (suppl 3):2–9.
Roberto Pellicciari et al., J. Med. Chem., 1996, 39, 2259–2269.
T. Saitoh et al., British Journal of Pharmacology (1998) 123, 771–779.

* cited by examiner

Primary Examiner—Floyd D. Higel
Assistant Examiner—Ebenezer Sackey
(74) Attorney, Agent, or Firm—Arvie J. Anderson

(57) ABSTRACT

Compounds of the formula

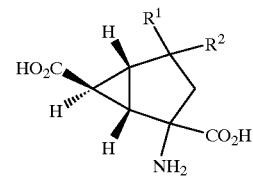

in which $R^1$ and $R^2$ are as defined in the specification, and non-toxic metabolically labile ester and amides thereof are useful as modulators of metabotropic glutamate receptor function.

7 Claims, No Drawings

HYDANTOIN DERIVATIVES

PRIORITY CLAIM

This application is a division of U.S. patent application Ser. No. 09/322,651 filed on May 28, 1999 now U.S. Pat. No. 6,160,009, which is a division of U.S. patent application Ser. No. 09/078,337 filed on May 13, 1998 now U.S. Pat. No. 5,958,960, which claims the benefit of U.S. Provisional Application 60/047,011, filed May 14, 1997.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.,* 21, 165 (1981); Monaghan, Bridges, and Cotman, *Ann. Rev. Pharmacol. Toxicol.,* 29, 365 (1989); Watkins, Krogsgaard-Larsen, and Honore, *Trans. Pharm. Sci.,* 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D or C, increases or decreases in c-AMP formation, and changes in ion channel function. Schoepp and Conn, *Trends in Pharmacol. Sci.,* 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.,* 11, 508 (1990); McDonald and Johnson, *Brain Research Reviews,* 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogenous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and anti-emetic agents.

International Patent Application Publication No. WO 96/05175 discloses the compound 2-aminobicyclo[3.1.0] hexane-2,6-dicarboxylic acid and its salts and esters as metabotropic glutamate receptor agonists.

SUMMARY OF THE INVENTION

The present invention provides a compound of formula

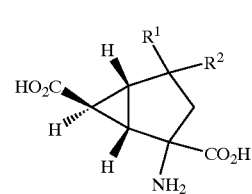

I in which:

(a) $R^1$ represents fluoro, $XOR^3$, $XNR^4R^5$, $SO_3H$, tetrazol-5-yl, CN or $PO_3R_2^6$ and $R^2$ represents hydrogen; or (b) $R^1$ and $R^2$ each represents fluoro; or (c) $R^1$ and $R^2$ together represent =O, =$NOR^7$ or =$CR^8R^9$; or (d) one of $R^1$ and $R^2$ represents amino and the other represents carboxyl; or (e) $R^1$ represents $N_3$, $(CH_2)_mCOOR^{3a}$, $(CH_2)_mPO_3R^{6a}{}_2$, $NHCONHR^{3b}$ or $NHSO_2R^{3c}$ and $R^2$ represents hydrogen; or (f) $R^1$ and $R^2$ together represent =$CHCOOR^{3b}$, =$CHPO_3R_2^{6a}$ or =CHCN; and $R^3$ represents a hydrogen atom; a (1–6C) alkyl group; a (3–6C)alkenyl group; a (3–6C)alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (3–6C)alkenyl or (3–6C)alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups;

$R^{3a}$, $R^{3b}$ and $R^{3c}$ are as defined for $R^3$;

X represents a bond, $CH_2$ or CO;

m represents an integer of from 1 to 3;

$R^4$ represents $COR^{10}$ or is as defined for $R^3$;

$R^5$, $R^7$, $R^8$, $R^9$ and $R^{10}$ are as defined for $R^3$;

$R^6$ represents hydrogen or a (1–6C)alkyl group; and $R^{6a}$ is defined for $R^6$;

or a non-toxic metabolically labile ester or amide thereof; or a pharmaceutically acceptable salt thereof.

The compounds of formula I are modulators of metabotropic glutamate receptor function, in particular agonists or antagonists of glutamate at metabotropic glutamate receptors.

According to another aspect, therefore, the present invention provides a method of modulating metabotropic glutamate receptor function in a mammal including a human, which comprises administering an effective amount of a compound of formula I, or a non-toxic metabolically labile ester or amide thereof, or a pharmaceutically acceptable salt thereof.

According to yet another aspect, the present invention provides the use of a compound of formula I as defined hereinabove for the manufacture of a medicament for use in modulating metabotropic glutamate receptor function.

It will be appreciated that the compounds of formula I contain at least four asymmetric carbon atoms; three being in the cyclopropane ring and one or two being in the cyclopentane ring. It will also be appreciated that compounds of formula I in which $R^1$ and $R^2$ together represent $=NOR^7$ may be in the syn or anti form, and that compounds of formula I in which $R^1$ and $R^2$ together represent $=CR^8R^9$, $=CHCOOR^{3b}$, $=CHPO_3R_2^{6a}$ or $=CHCN$ may be in the (E) or (Z) form. The present invention includes all stereoisomeric forms of the compounds of formula I, including each of the individual enantiomers and mixtures thereof.

The present invention also includes all physical forms of the compounds of formula I, including crystalline solvates.

DETAILED DESCRIPTION AND PREFERRED EMBODIMENTS

Preferably the compounds of formula I have the configuration Ia or Ib shown below

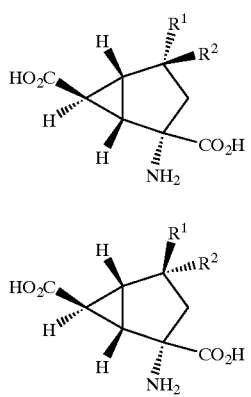

Unless specified otherwise, the term "alkyl" as used herein means a straight chain or branched alkyl group. Examples of values for a (1–6C)alkyl group include (1–4C) alkyl such as methyl, ethyl, propyl, isopropyl, butyl and isobutyl.

The term (3–6C)alkenyl includes (3–4C)alkenyl such as allyl.

The term (3–6C)alkynyl includes (3–4C)alkynyl such as propynyl.

The term heteroaromatic group includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or a 5–6 membered ring containing from one to four heteroatoms selected from oxygen, sulfur and nitrogen. Examples of heteroaromatic groups are furyl, thiophenyl, oxazolyl, isoxazolyl, thiazoyl, isothiazolyl, imidazolyl, pyrimidyl, benzofuryl, benzothiophenyl, benzimidazolyl, benzoxazolyl, benzothiazolyl and indolyl.

The term aromatic group includes phenyl and a polycyclic aromatic carbocyclic ring such as 1-naphthyl or 2-naphthyl.

The term "optionally substituted", as used in the term "optionally substituted heteroaromatic or aromatic group", herein signifies that one, two or more substituents may be present, said substituents being selected from atoms and groups which, when present in the compound of formula I, do not prevent the compound of formula I from functioning as a modulator of metabotropic glutamate receptor function.

Examples of atoms and groups which may be present in an optionally substituted heteroaromatic or aromatic group are amino, hydroxy, nitro, halogeno, (1–6C) alkyl, (1–6C) alkoxy, (1–6C)alkylthio, carboxy, (1–6C) alkoxycarbonyl, carbamoyl, (1–6C) alkanoylamino, (1–6C)alkylsulphonyl, (1–6C) alkylsulphonylamino, (1–6C)alkanoyl, phenyl, phenoxy, phenylthio, phenylsulphonyl, phenylsulphonylamino, toluenesulphonylamino, and (1–6C) fluoroalkyl. Examples of particular values are amino, hydroxy, nitro, fluoro, chloro, bromo, iodo, methyl, methoxy, methylthio, carboxy, acetylamino, methanesulphonyl, methanesulphonylamino, acetyl, phenyl, phenoxy, phenylthio, phenylsulphonyl, and trifluoromethyl.

Examples of values for an optionally substituted aromatic group are 1-naphthyl, 2-naphthyl, phenyl, 2-biphenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,4-difluorophenyl, 3,4-difluorophenyl, pentafluorophenyl, 2-chlorophenyl, 3-chlorophenyl, 4-chlorophenyl, 2,4-dichlorophenyl, 3,4-dichlorophenyl, 3,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,5-dimethoxyphenyl, 3,4-dimethoxyphenyl, 3,5-dimethoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluorophenyl, 2-fluoro-5-trifluoromethylphenyl, 2-phenoxyphenyl, 3-phenoxyphenyl, 3-carboxyphenyl, and 4-carboxyphenyl.

The term "non-aromatic carbocyclic group" includes a monocyclic group, for example a (3–10C)cycloalkyl group, such as cyclopropyl, cyclobutyl, cyclopentyl, cyclohexyl, cycloheptyl, cyclooctyl, cyclononyl or cyclodecyl, and a fused polycyclic group such as 1-adamantyl or 2-adamantyl, 1-decalyl, 2-decalyl, 4a-decalyl, bicyclo[3,3,0]oct-1-yl, -2-yl or -3-yl, bicyclo[4,3,0]non-1-yl, -2-yl, -3-yl or -7-yl, bicyclo[5,3,0]dec-1-yl, -2-yl, -3-yl, -4-yl, -8-yl or -9-yl and bicyclo[3.3.1]non-1-yl, -2-yl, -3-yl or 9-yl.

The term "non-aromatic heterocyclic group" includes a 4 to 7 membered ring containing one or two heteroatoms selected from oxygen, sulphur and nitrogen, for example azetidin-1-yl or -2-yl, pyrrolidin-1-yl, -2-yl or -3-yl, piperidin-1-yl, -2-yl, -3-yl or -4-yl, hexahydroazepin-1-yl, -2-yl, -3-yl or -4-yl, oxetan-2-yl or -3-yl, tetrahydrofuran-2-yl or -3-yl, tetrahydropyran-2-yl, -3-yl or -4-yl, hexahydrooxepin-2-yl, -3-yl or -4-yl, thietan-2-yl or -3-yl, tetrahydrothiophen-2-yl or -3-yl, tetrahydrothiopyran-2-yl, -3-yl or -4-yl, hexahydrothiepin-2-yl, -3-yl or -4-yl, piperazin-1-yl or -2-yl, morpholin-1-yl, -2-yl or -3-yl, thiomorpholin-1-yl, -2-yl or -3-yl, tetrahydropyrimidin-1-yl, -2-yl, -4-yl or -5-yl, imidazolin-1-yl, -2-yl or -4-yl, imidazolidin-1-yl, -2-yl or -4-yl, oxazolin-2-yl, -3-yl, -4-yl or -5-yl, oxazolidin-2-yl, -3-yl, -4-yl or -5-yl, thiazolin-2-yl, -3-yl, -4-yl or -5-yl, or thiazolidin-2-yl, -3-yl, -4-yl or -5-yl.

The term "a non-aromatic monocyclic carbocyclic group fused with one or two monocyclic aromatic or heteroaromatic groups" includes a (3–10C)cycloalkyl group fused with a benzene ring or a an aromatic 5–6 membered ring containing from one to four heteroatoms selected from oxygen, sulfur and nitrogen, such as indanyl, 1,2,3,4-tetrahydronaphth-1-yl or -2-yl, 5,6,7,8-tetrahydroquinolin-5-yl, -6-yl, -7-yl or 8-yl, 5,6,7,8-tetrahydroisoquinolin-5-yl, -6-yl, -7-yl or 8-yl, 4,5,6,7-tetrahydrobenzothiophen-4-yl, -5-yl, -6-yl or -7-yl, dibenzo[2,3,6,7]cycloheptan-1-yl or -4-yl, dibenzo[2,3,6,7]cyclohept-4-en-1-yl or -4-yl, or 9-fluorenyl.

The term "a non-aromatic monocyclic heterocyclic group fused with one or two monocyclic aromatic or heteroaromatic groups" includes a 4 to 7 membered ring containing one or two heteroatoms selected from oxygen, sulphur and nitrogen, fused with a benzene ring or a an aromatic 5–6 membered ring containing from one to four heteroatoms selected from oxygen, sulfur and nitrogen, such as 2,3-dihydrobenzopyran-2-yl, -3-yl or -4-yl, xanthen-9-yl, 1,2,3,4-tetrahydroquinolin-1-yl, -2-yl, -3-yl or -4-yl, 9,10-dihydroacridin-9-yl or -10-yl, 2,3-dihydrobenzothiopyran-2-yl, -3-yl or -4-yl, or dibenzothiopyran-4-yl.

Examples of values for $R^3$ when it represents a (1–6C) alkyl group are methyl, ethyl, propyl, isopropyl, butyl and isobutyl.

An example of a value for $R^3$ when it represents a (3–6C) alkenyl group is allyl.

An example of a value for $R^3$ when it represents a (3–6C) alkynyl group is propynyl.

When $R^3$ represents an optionally substituted aromatic group, it preferably represents a 2-naphthyl group or a phenyl group which is unsubstituted or substituted by one or two substituents selected independently from halogen, (1–4C) alkyl and (1–4C) alkoxy.

Examples of values for $R^3$ when it represents an optionally substituted aromatic group are 2-naphthyl, phenyl, 2-fluorophenyl, 3-fluorophenyl, 4-fluorophenyl, 3,4-difluorophenyl, pentafluorophenyl, 2-chlorophenyl, 3-chlorophenyl, 4-chlorophenyl, 3,4-dichlorophenyl, 2,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 3-trifluoromethylphenyl and 4-trifluoromethylphenyl.

Examples of values for $R^3$ when it represents a substituted (1–6C)alkyl, (2–6C)alkenyl or (2–6C)alkynyl group are phenyl (1–4C)alkyl and diphenyl (1–4C)alkyl groups which are unsubstituted or substituted on phenyl by one or two of halogen, (1–4C)alkyl and (1–4C)alkoxy, for example benzyl, 2-phenylethyl, 2-phenylpropyl, and 2-thiophenylmethyl. Other examples are (3–6C)cycloalkyl (1–4C)alkyl groups, such as cyclopropylmethyl.

An example of a value for $R^3$ when it represents an optionally substituted heteroaromatic group is 2-pyrimidyl.

Examples of particular values for $R^{3a}$ are hydrogen and (1–6C)alkyl, such as methyl or ethyl.

Examples of particular values for $R^{3b}$ are hydrogen and (1–6C)alkyl, such as methyl or ethyl.

Examples of particular values for $R^{3c}$ are (1–6C)alkyl such as methyl.

Examples of more particular values for $R^4$ are hydrogen, (1–6C)alkanoyl such as acetyl, benzoyl, (1–6C)alkyl such as methyl and (3–6C)cycloalkyl(1–4C)alkyl such as cyclopropylmethyl.

Examples of more particular values for $R^5$ are hydrogen, (1–6C)alkyl such as methyl and (3–6C)cycloalkyl(1–4C) alkyl, such as cyclopropylmethyl.

Examples of particular values for $R^6$ are hydrogen, methyl and ethyl.

Examples of particular values for $R^{6a}$ are hydrogen, methyl and ethyl.

Examples of more particular values for $R^7$, $R^8$, $R^9$ and $R^{10}$ are hydrogen, (1–6C)alkyl such as methyl and optionally substituted aromatic such as phenyl.

A particular group of compounds according to the invention are those in which (a) $R^1$ represents fluoro, $XOR^3$, $XNR^4R^5$, $SO_3H$, tetrazol-5-yl, CN or $PO_3R_2^6$ and $R^2$ represents hydrogen; or (b) $R^1$ and $R^2$ each represents fluoro; or (c) $R^1$ and $R^2$ together represent =O, =$NOR^7$ or =$CR^8R^9$; or (d) one of $R^1$ and $R^2$ represents amino and the other represents carboxyl.

Particular values for $R^1$ and $R^2$ are:

(a) $R^1$ represents fluoro; $XOR^3$; $XNR^4R^5$; $SO_3H$; tetrazol-5-yl; CN or $PO_3H_2$; X represents a bond, CO or $CH_2$; $R^3$ represents a hydrogen atom or a (1–6C)alkyl group; a phenyl group which is unsubstituted or substituted by one or two substituents selected independently from halogen, (1–4C)alkyl and (1–4C)alkoxy; a phenyl (1–4C)alkyl or diphenyl (1–4C)alkyl group which is unsubstituted or substituted on phenyl by one or two substituents selected from halogen, (1–4C)alkyl and (1–4C)alkoxy; $R^4$ represents hydrogen, (1–6C) alkanoyl, benzoyl, (3–6C)cycloalkyl(1–4C)alkyl or (1–6C)alkyl; and $R^5$ represents hydrogen, (3–6C) cycloalkyl(1–4C)alkyl or (1–6C)alkyl; and $R^2$ represents hydrogen; or (b) $R^1$ and $R^2$ each represents fluoro; or (c) $R^1$ and $R^2$ together represent =O, =NOH, or =$CR^8R^9$ in which each of $R^8$ and $R^9$ independently represents a hydrogen atom, a (1–6C)alkyl group or a phenyl group which is unsubstituted or substituted by one or two substituents selected from halogen, (1–4C) alkyl and (1–4C) alkoxy; or (d) one of $R^1$ and $R^2$ represents amino and the other represents carboxyl; or (e) $R^1$ represents $N_3$, $CH_2COOR^{3a}$, $CH_2PO_3R_2^{6a}$, $NHCONHR^{3b}$ or $NHSO_2R^{3c}$; $R^{3a}$ represents hydrogen or (1–6C)alkyl; $R^{3b}$ represents (1–6C)alkyl; $R^{3c}$ represents (1–6C)alkyl; $R^2$ represents hydrogen; and each of $R^{6a}$ independently represents hydrogen or (1–6C)alkyl; or (f) $R^1$ and $R^2$ together represent =CHCOOH, =$CHPO_3H_2$, =$CHPO_3(C_2H_5)_2$ or =CHCN.

Within this group, particular values for $R^1$ and $R^2$ are:

(a) $R^1$ represents fluoro; $XOR^3$; $XNR^4R^5$; $SO_3H$; tetrazol-5-yl; CN or $PO_3H_2$; X represents a bond, $CH_2$ or CO; $R^3$ represents a hydrogen atom; a (1–6C)alkyl group; a phenyl group which is unsubstituted or substituted by one or two substituents selected independently from halogen, (1–4C)alkyl and (1–4C)alkoxy; a phenyl (1–4C)alkyl or diphenyl(1–4C)alkyl group which is unsubstituted or substituted on phenyl by one or two substituents selected from halogen, (1–4C)alkyl and (1–4C)alkoxy; $R^4$ represents hydrogen, (1–6C) alkanoyl or (1–6C)alkyl, and $R^5$ represents hydrogen or (1–6C)alkyl; and $R^2$ represents hydrogen; or (b) $R^1$ and $R^2$ each represents fluoro; or (c) $R^1$ and $R^2$ together represent =O, =NOH, or =$CR^8R^9$ in which each of $R^8$ and $R^9$ independently represents a hydrogen atom, a (1–6C)alkyl group or a phenyl group which is unsubstituted or substituted by one or two substituents selected independently from halogen, (1–4C) alkyl and (1–4C) alkoxy; or (d) one of $R^1$ and $R^2$ represents amino and the other represents carboxyl.

Preferably $R^1$ represents fluoro, hydroxyl, $PO_3H_2$, methoxy, amino, azido, acetylamino, benzoylamino, methanesulfonylamino, methylaminocarbonylamino, N,N-dicyclopropylmethyl, carboxy, cyano or carboxamido and $R^2$ represents hydrogen, or $R^1$ and $R^2$ together represent =O, =NOH, =$CHCO_2H$, =$CH_2$, =$CHPO_3(C_2H_5)_2$, =$CHPO_3H_2$ or =CHCN.

Examples of compounds of formula I include: 2-amino-4-hydroxybicyclo[3.1.0]hexane-2,6-dicarboxylic acid; 2-amino-4-fluorobicyclo[3.1.0]hexane-2,6-dicarboxylic acid; 2-amino-4,4-difluorobicyclo[3.1.0]hexane-2,6-dicarboxylic acid; 2-amino-4-carboxybicyclo[3.1.0]hexane-2,6-dicarboxylic acid; 2,4-diaminobicyclo[3.1.0]hexane-2,6-dicarboxylic acid; 2-amino-4-aminomethylbicyclo[3.1.0] hexane-2,6-dicarboxylic acid; 2-amino-4-acetylaminomethylbicyclo[3.1.0]hexane-2,6-dicarboxylic acid; 2-amino-4-oxobicyclo[3.1.0]hexane-2,6-dicarboxylic acid; 2-amino-4-hydroxyiminobicyclo[3.1.0]hexane-2,6-dicarboxylic acid; 2-amino-4-phosphonobicyclo[3.1.0] hexane-2,6-dicarboxylic acid; 2-amino-4-methoxybicyclo [3.1.0]hexane-2,6-dicarboxylic acid; 2-amino-4-azidobicyclo[3.1.0]hexane-2,6-dicarboxylic acid; 2-amino-4-benzoylaminobicyclo[3.1.0]hexane-2,6-dicarboxylic acid; 2-amino-4-methanesulfonylaminobicyclo[3.1.0]hexane-2, 6-dicarboxylic acid; 2-amino-4-methylaminocarbonylaminobicyclo[3.1.0]hexane-2,6-dicarboxylic acid; 2-amino-4-(N,N-dicyclopropylmethyl) aminobicyclo[3.1.0]hexane-2,6-dicarboxylic acid; 2-amino-4-carboxymethylenebicyclo[3.1.0]hexane-2,6-dicarboxylic acid; 2-amino-4-methylenebicyclo[3.1.0]hexane-2,6-dicarboxylic acid; 2-amino-4-diethylphosphonomethylenebicyclo[3.1.0]hexane-2,6-dicarboxylic acid; 2-amino-4-phosphonomethylenebicyclo [3.1.0]hexane-2,6-dicarboxylic acid; 2-amino-4-cyanomethylenebicyclo[3.1.0]hexane-2,6-dicarboxylic acid; 2-amino-4-cyanobicyclo[3.1.0]hexane-2,6-dicarboxylic acid and 2-amino-4-carboxamidobicyclo [3.1.0]hexane-2,6-dicarboxylic acid.

Particularly preferred compounds of formula I are (1S*, 2S*,5R*,6R*)-2-amino-4-oxobicyclo[3.1.0]hexane-2,6-dicarboxylic acid; (1S*,2S*,5R*,6R*)-2-amino-4-[anti]-hydroximinobicyclo[3.1.0]hexane-2,6-dicarboxylic acid; (1S*,2S*,5R*,6R*)-2-amino-4-[syn]-hydroximinobicyclo [3.1.0]hexane-2,6-dicarboxylic acid; (1S*,2R*,4S*,5S*, 6S*)-2-amino-4-fluorobicyclo[3.1.0]hexane-2,6-dicarboxylic acid; (1S*,2S*,5R*,6S*)-2-amino-4-Z-carboxymethylenebicyclo[3.1.0]hexane-2,6-dicarboxylic acid and (1S*,2S*,5R*,6S*)-2-amino-4-methylenebicyclo [3.1.0]hexane-2,6-dicarboxylic acid. These compounds have been found to process especially high potency as metabotropic glutamate receptor modulators.

The present invention includes pharmaceutically acceptable salts of the formula I compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, butyne-1,4-dioate, hexane-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, a-hydroxybutyrate, glycolate, maleate, tartrate, methanesulfonate, propanesulfonate, naphthalene-1-sulfonate, naphthalene-2-sulfonate, mandelate, magnesium, tetramethylammonium, potassium, trimethylammonium, sodium, methylammonium, calcium, and the like salts.

Pharmaceutically acceptable metabolically labile ester and amide of compounds of formula I are ester or amide derivatives of compounds of formula I that are hydrolyzed in vivo to afford said compound of formula I and a pharmaceutically acceptable alcohol or amine. Examples of metabolically labile esters include esters formed with (1–6C) alkanols in which the alkanol moiety may be optionally substituted by a (1–8C) alkoxy group, for example methanol, ethanol, propanol and methoxyethanol. Example of metabolically labile amides include amides formed with amines such as methylamine.

According to another aspect, the present invention provides a process for the preparation of a compound of formula I which comprises (a) hydrolyzing a compound of formula

II

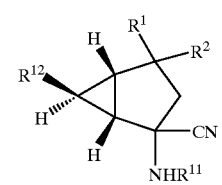

in which $R^{11}$ represents a hydrogen atom or an acyl group and $R^{12}$ represents a carboxyl group or an esterified carboxyl group, or a salt thereof;

(b) hydrolyzing a compound of formula

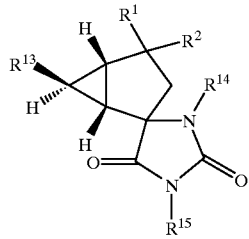

III in which $R^{13}$ represents a carboxyl group or an esterified carboxyl group, and $R^{14}$ and $R^{15}$ each independently represent a hydrogen atom, a (2–6C) alkanoyl group, a (1–4C) alkyl group, a (3–4C) alkenyl group or a phenyl (1–4C) alkyl group in which the phenyl is unsubstituted or substituted by halogen, (1–4C) alkyl or (1–4C) alkoxy, or a salt thereof; or (c) deprotecting a compound of formula

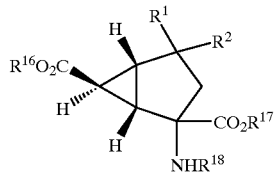

IV in which $R^{18}$ represents a hydrogen atom or a nitrogen protecting group and each of $R^{16}$ and $R^{17}$ independently represents a hydrogen atom or a carboxyl protecting group, or a salt thereof;

whereafter, if necessary and/or desired (i) resolving the compound of formula I;

(ii) converting the compound of formula I into a non-toxic metabolically labile ester or amide thereof; and/or;

(iii) converting the compound of formula I or a non-toxic metabolically labile ester or amide thereof into a pharmaceutically acceptable salt thereof.

The protection of carboxylic acid and amine groups is generally described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include alkyl groups such as methyl, ethyl, t-butyl, and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl. Examples of amine protecting groups include acyl groups, such as groups of formula $R^aCO$ in which $R^a$ represents (1–6C) alkyl, (3–10C) cycloalkyl, phenyl(1–6C) alkyl, phenyl, (1–6C) alkoxy, such as t-butoxy, phenyl(1–6C)alkoxy, or a (3–10C) cycloalkoxy, wherein a phenyl group may optionally be substituted by one or two substituents independently selected from amino, hydroxy, nitro, halogeno, (1–6C) alkyl, (1–6C) alkoxy, carboxy, (1–6C) alkoxycarbonyl, carbamoyl, (1–6C) alkanoylamino, (1–6C) alkylsulphonylamino, phenylsulphonylamino, toluenesulphonyl-amino, and (1–6C)fluoroalkyl.

Preferred values for $R^{11}$ are hydrogen, (2–6C)alkanoyl groups, such as acetyl and t-butoxycarbonyl.

Preferred values for $R^{12}$ and $R^{13}$ when they represent esterified carboxyl groups are (1–6C)alkoxycarbonyl groups such as ethoxycarbonyl.

Preferred values for $R^{14}$ and $R^{15}$ are independently hydrogen or benzyl.

Preferred values for $R^{16}$ and $R^{17}$ are methyl and ethyl.

A preferred value for $R^{18}$ is t-butoxycarbonyl.

The compounds of formula II are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water and at a temperature in the range of from 50 to 200° C.

The compounds of formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 50 to 150° C.

The compounds of formula IV may be deprotected by a conventional method. Thus, an alkyl carboxyl protecting group may be removed by hydrolysis. The hydrolysis may conveniently be performed by heating the compound of formula IV in the presence of either a base, for example an alkali metal hydroxide such as lithium, sodium or potassium hydroxide, or an alkaline metal hydroxide, such as barium hydroxide, or an acid such as hydrochloric acid. The hydrolysis is conveniently performed at a temperature in the range of from 10 to 300° C. An aralkyl carboxyl protecting group may conveniently be removed by hydrogenation. The hydrogenation may conveniently be effected by reacting the compound of formula IV with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0 to 100° C. An acyl, amine protecting group is also conveniently removed by hydrolysis, for example as described for the removal of an alkyl carboxyl protecting group. A t-butoxycarbonyl group is conveniently removed using anhydrous hydrogen chloride in a solvent such as ethyl acetate.

The compounds of formula II may be prepared by reacting a compound of formula V

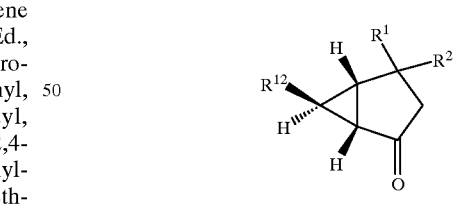

V with an alkali metal cyanide, such as lithium, sodium or potassium cyanide, and an ammonium halide, such as ammonium chloride. It has been found advantageous to perform the reaction in the presence of ultrasound. Thus, the ammonium halide and alkali metal cyanide are advantageously mixed with chromatography grade alumina in the presence of a suitable diluent such as acetonitrile. The mixture is then irradiated with ultrasound, whereafter the compound of formula V is added, and the mixture is again irradiated.

The resultant mixture of diastereoisomeric amino-nitriles may then be reacted with an acylating agent, such as acetyl chloride in the presence of a suitable base, for example an amine such as diisopropylethylamine and in the presence of a suitable solvent such as dichloromethane to afford a mixture of diastereomeric acylamino nitriles. The desired diastereoisomer may conveniently be separated from this mixture, for example by chromatography.

The compounds of formula III may be prepared by reacting a compound of formula V with a alkali metal cyanide, such as lithium, sodium or potassium cyanide, and ammonium carbonate in an aqueous alcohol, such as aqueous ethanol. Conveniently the reaction is performed at a temperature in the range of from 35 to 150° C. If desired, the compounds of formula III may then be alkylated or acylated for example using an appropriate compound of formula $R^{14}Cl$ or Br and/or $R^{15}Cl$ or Br.

Alternatively, the compounds of formula III may be prepared from a compound of formula

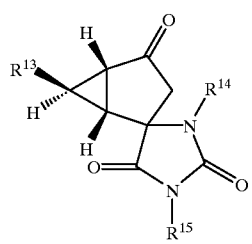

VI by procedures analagous to methods well known in the art.

Thus, for example, a compound of formula III in which $R^1$ represents α-hydroxy and $R^2$ represents hydrogen may be prepared by reacting a compound of formula VI with a reducing agent, such as sodium borohydride.

Compounds of formula II, III or IV in which $R^1$ represents $OR^3$ other than hydroxy and $R^2$ represents hydrogen may be prepared by reacting the corresponding compound of formula II, III or IV in which $R^1$ represents hydroxy with a compound of formula $R^J Z^1$ in which $Z^1$ represents a leaving atom or group, such as a chlorine, bromine or iodine atom or a p-toluenesulfonyloxy group, in the presence of a base, such as sodium hydride or potassium t-butoxide. The reaction is conveniently performed at a temperature in the range of from 0 to 100° C. Suitable solvents include amides such as dimethylformamide, sulfoxides such as dimethylsulfoxide and ethers such as tetrahydrofuran. Alternatively, the compound may be prepared by employing Mitsunobu chemistry, as described in *Bull. Chem. Soc.* Japan, 40, 2380, 1967.

Compounds of formula II, III or IV in which $R^1$ and $R^2$ both represent fluoro may be prepared by reacting the corresponding compound of formula II, III or IV in which $R^1$ and $R^2$ together represent=O respectively with a fluorinating agent such as diethylaminosulfur trifluoride or dimethylaminosulfur trifluoride, according to the method described in *J. Org. Chem*, 50, 1599, 1985 and *Tet. Lett.*, 34(31), 4917, 1993. The reaction is conveniently performed in a solvent such as dichloromethane or tetrahydrofuran at a temperature in the range of from 0 to 50° C. Alternative fluorinating agents are hydrogen fluoride in trifluoroacetic acid and $CF_2Br_2$ with zinc dust (*J. Chem. Soc.* Perk. Trans. 1, 3, 335, 1993). Alternatively, the compounds of formula II, III or IV in which $R^1$ and $R^2$ together represent=O may be converted to a dithiolane by reaction with $H_2SCH_2CH_2SH$, followed by reaction with $BF_3$-acetic acid complex (*J. Org. Chem.*, 51, 3508, 1986).

Compounds of formula II, III or IV in which $R^1$ and $R^2$ together represent =$NOR^6$ may be prepared by reacting the corresponding compound of formula II, III or IV with a hydroxylamine of formula $H_2NOR^6$, or an acid addition salt thereof, such as a hydrochloride, in the presence of a base, such as sodium hydroxide, sodium acetate or triethylamine. The reaction is conveniently performed at a temperature in the range of from 0 to 50° C. in the presence of a polar solvent, such as ethanol, aqueous ethanol or dimethylsulfoxide.

Compounds of formula II, III or IV in which $R^1$ represents amino and $R^2$ represents hydrogen may be prepared by reducing a corresponding compound of formula II, III or IV in which $R^1$ and $R^2$ together represent =NOH. Suitable reducing agents include hydrogen in the presence of a noble metal catalyst, such as palladium on charcoal or Raney nickel, lithium aluminum hydride, borane or zinc with acetic acid. Alternatively, they may be prepared by reducing a compound of formula II, III or IV in which $R^1$ represents azido and $R^2$ represents hydrogen. The reduction is conveniently performed using triphenylphosphine in the presence of aqueous tetrahydrofuran at a temperature in the range of from 0 to 100° C.

Compounds of formula II, III or IV in which $R^1$ represents $NH_2$ may be alkylated or acylated to afford a corresponding compound of formula II, III or IV in which $R^1$ represents $NR^4R^5$, for example by alkylation using a compound for formula $R^4Z^2$ or $R^5Z^3$ in which $Z^2$ and $Z^3$ represent leaving atoms or groups such as a chlorine atom or a p-toluenesulfonyloxy group; by reductive alkylation using an aldehyde or ketone and a reducing agent such as sodium cyanoborohydride, or by acylation using an acyl halide or anhydride.

Compounds of formula II, III or IV in which $R^1$ represents $NHCONHR^{3b}$ may be prepared by reacting a corresponding compound of formula II, III or IV in which $R^1$ represents amino with an isocyanate of formula $R^{36}$—N=C=O. Convenient solvents include dichloromethane.

Compounds of formula II, III or IV in which $R^1$ represents $NHSO_2R^{3c}$ may be prepared by reacting a corresponding compound of formula II, III or IV in which $R^1$ represents amino with a sulfonyl halide of formula $R^{3c}SO_2Z^4$ in which $Z^4$ is, for example, chlorine or bromine. The reaction is conveniently performed in the presence of a base, such as triethylamine and in a solvent such as dichloromethane.

Compounds of formula II, III or IV in which $R^1$ represents fluoro and $R^2$ represents hydrogen may be prepared by reacting a corresponding compound of formula II, III or IV in which $R^1$ represents hydroxyl and $R^2$ represents hydrogen with diethylaminosulfur trifluoride or dimethylaminosulfur trifluoride according to the method described in *Tet. Assym.*, 4(2), 161, 1994. The reaction is conveniently performed at a temperature in the range of from 20 to 50° C., in the presence of a solvent such as methylene chloride, toluene or tetrahydrofuran. Alternatively, the alcohol may be reacted with caesium fluoride and tetrabutylammonium fluoride in the presence of a base such as triethylamine, according to the method described in *Syn.*, 3, 273, 1994. Another convenient fluorinating agent is poly(4-vinylpyridinium)polyhydrogen fluoride (Syn. Lett., 5, 267, 1990).

Compounds of formula II, III or IV in which $R^1$ represents CN or azido may be prepared by reacting the corresponding compound of formula II, III or IV in which $R^1$ represents hydroxyl with a hydrocarbonylsulfonyl halide such as p-toluenesulfonyl chloride or methanesulfonyl chloride, for example in pyridine as reaction solvent, followed by a cyanide salt such as potassium cyanide, or an azide salt, such as sodium azide, for example in dimethylsulfoxide as reaction solvent.

Compounds of formula II, III or IV in which $R^1$ represents carboxy may be prepared by hydrolyzing the corresponding nitrile. The resultant carboxy compound may then, if desired, be esterified or converted into an amide of formula $CONR^4R^5$ by conventional methods.

Compounds of formula II, III or IV in which $R^1$ represents $CH_2NR^4R^5$ may be prepared by reducing the corresponding nitrile, for example by hydrogenation in the presence of palladium on charcoal or Raney nickel, followed if necessary by alkylation, reductive alkylation or acylation as described above.

Compounds of formula III or IV in which $R^1$ represents a tetrazolyl group may be prepared by reacting a corresponding compound of formula III or IV in which $R^1$ represents CN with an azide such as tetrabutyl triazide.

The compounds of formula VI may be prepared by reacting a compound of formula

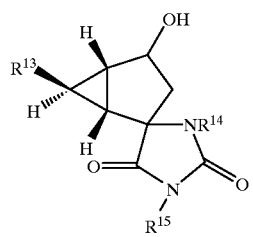

VII with an oxidizing agent, for example Jones reagent ($CrO_3$, $H_2SO_4$).

The compounds of formula VII may be prepared by reacting a compound of formula

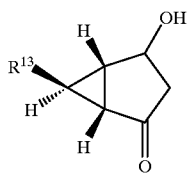

VIII with an alkali metal cyanide, such as potassium cyanide, and ammonium carbonate, followed if desired by alkylation or acylation using a compound of formula $R^{14}Br$ or $R^{15}Br$.

Compounds of formula II, III or IV in which $R^1$ and $R^2$ together represent $=CR^8R^9$ may be prepared from the corresponding compounds of formula II, III or IV in which $R^1$ and $R^2$ together represents =O by a Wittig reaction, for example by reaction with a compound of formula $Ph_3P=CR^8R^9$ which may be formed by reacting triphenylphosphine with an alkyl halide.

Compounds of formula II, III or IV in which $R^1$ and $R^2$ together represent $=CHCOOR^{3b}$, $=CHPO_3R^{6a}{}_2$ or $=CHCN$ may be prepared from a corresponding compound of formula II, III or IV in which $R^1$ and $R^2$ together represent =O by a Wadsworth-Emmons reaction, for example by reaction with an alkali metal salt of a dialkyl phosphono acetate ester, such as the sodium salt of benzyl diethylphosphonoacetate, a tetraalkyl methylenediphosphonate, such as tetraalkyl methylenediphosphonate or of a dialkyl cyanomethylphosphonate, such as the sodium salt of diethyl cyanomethylphosphonate. The reaction is conveniently performed in an anhydrous solvent such as anhydrous toluene. An alkyl group represented by $R^{6a}$ may be removed by hydrolysis, for example using an acid such as trifluoroacetic acid or hydrochloric acid.

Compounds of formula II, III or IV in which $R^1$ and $R^2$ together represent $(CH_2)_mPO_3R^{6a}{}_2$ may be prepared from corresponding compound of formula II, III or IV in which $R^1$ and $R^2$ together represent $=CHPO_3R^{6a}{}_2$ by reduction, for example by catalytic hydrogenation in the presence of a Group VIII metal catalyst, such as palladium-on-charcoal.

The compounds of formula VIII may be prepared by reacting a compound of formula

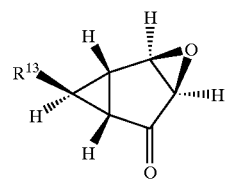

IX with a thiol, such as N-acetyl-L-cysteine, a base, such as sodium borate and a diaryldiselenide, such as diphenyldiselenide.

The compounds of formula IX may be prepared by reacting a compound of formula

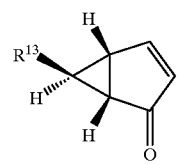

X with a peroxide, such as tert-butyl hydroperoxide.

The compounds of formula V in which $R^1$ represents $PO_3R^6{}_2$ and each $R^6$ represents (1–6C)alkyl may be prepared by reacting a compound of formula X with a trialkylphosphite, such as triethylphosphite, in the presence of a phenol.

Compounds of formula III, IV or V in which $R^1$ represents $SO_3H$ and $R^2$ represents hydrogen may be prepared by oxidizing the corresponding compound of formula III, IV or V in which $R^1$ represents SH and $R^2$ represents hydrogen, for example using hydrogen peroxide and sulfuric acid (*Chem. Pharm. Bull.* 1971, 19, 2222), nitric acid (*J. Org. Chem.*, 1961, 26, 82) or hydrogen peroxide and acetic acid (*Helv. Chem. Acta* 1968, 349, 323).

Compounds of formula III, IV or V in which $R^1$ represents SH may be prepared by debenzylating the corresponding compound of formula III, IV or V in which $R^1$ represents benzylthio by reaction with sodium in liquid ammonia (*Angew. Chem.* 1967, 6, 698; *Org. Syn.*, 1986, 65, 215).

Compounds of formula V in which $R^1$ represents benzylthio may be prepared by reacting a compound of formula X with benzenethiol in the presence of a base, such as triethylamine.

It will be appreciated that the compounds of formula VIII correspond with the compounds of formula V in which $R^1$ represents hydroxy and $R^2$ represents hydrogen. Other compounds of formula V may be prepared from the compounds of formula VIII by protecting the keto group and then converting the resultant protected compound into a compound of formula V by procedures analagous to methods well known in the art.

The compounds of formula X may be prepared by reacting a compound of formula XI

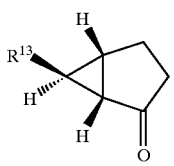

with iodotrimethyl silane in the presence of triethylamine to afford a silyl enol ether, and then reacting the silyl enol ether with palladium acetate. Alternatively, they may be prepared by reacting a compound of formula XI with allyl methyl carbonate in the presence of palladium(II) acetate. The reaction is conveniently performed in anhydrous acetonitrile.

The compounds of formula XI are known and may be prepared by reacting 2-cyclopenten-1-one with a carboxy protected (dimethyl sulfuranylidene) acetate. Suitable solvents for the reaction include aromatic hydrocarbons, such as toluene. The desired diastereomeric product may be isolated by chromatography.

The compounds of formula IV may be prepared by protecting a compound of formula I, for example by reaction with an alcohol such as ethanol in the presence of a dehydrating agent, such as thionyl chloride, to protect the carboxyl groups,, and reacting the resultant ester with $Boc_2O$ to protect the amino group. Compounds of formula IV in which $R^1$ and $R^2$ together represent =O may be converted into the corresponding compounds of formula IV by procedures analagous to methods well known in the art.

The compounds of formula I may be resolved using conventional methods, for example by forming a crystalline salt with an optically active acid or base. Alternatively, optically active starting materials may be used to prepare compounds of formula I in optically pure form.

The compounds of formula II, III and IV are believed to be novel, and are provided as further aspects of the invention.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis (ALS), AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable metabolically labile ester or amide thereof, or a pharmaceutically acceptable salt thereof.

The formula I compounds of the present invention are also believed to have the ability to treat a variety of other neurological disorders in mammals that are associated with glutamate dysfunction, including muscular spasms, convulsions, migraine headaches, urinary incontinence, nicotine withdrawal, psychosis, (such as schizophrenia) opiate tolerance and withdrawal, anxiety, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester or amide thereof, or a pharmaceutically acceptable salt thereof.

The ability of compounds to modulate metabotropic glutamate receptor function may be demonstrated by examining their ability to influence either cAMP production (mGluR 2, 3, 4, 6, 7 or 8) or phosphoinositide hydrolysis (mGluR 1 or 5) in cells expressing these individual human metabotropic glutamate receptor (mGluR) subtypes. (D. D. Schoepp, et al., *Neuropharmacol.*, 1996, 35, 1661–1672 and 1997, 36, 1–11).

The compounds of the present invention are preferably formulated prior to administration. Therefore, another aspect of the present invention is a pharmaceutical formulation comprising a compound of formula I and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
Tablets each containing 60 mg of active ingredient are made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

The following Examples further illustrate the compounds of the present invention and the methods for their synthesis.

The following abbreviations are used in the following: EtOAc, ethyl acetate; THF, tetrahydrofuran; Boc, t-butoxycarbonyl; Boc$_2$O, t-butoxycarboxylic acid anhydride; EtOH, ethanol; Et$_2$O, diethyl ether; DBU, 1,8-diazabicyclo[5.4.0]-undec-7-ene; and FDMS, field desorption mass spectrometry.

Preparation 1

Carboethoxymethyl Dimethylsulfonium Bromide

A solution of ethyl bromoacetate (265 g) and dimethyl sulfide (114 g) in acetone (500 mL) was stirred at room temperature. After three days, the title compound was isolated by filtration of the reaction mixture. Melting point 88–90° C.

Preparation 2

(1S*,5R*,6S*) Ethyl 2-Oxobicyclo[3.1.0]hexane-6-carboxylate

A suspension of carboethoxymethyl dimethylsulfonium bromide (45.5 g, 198.6 mmol) in toluene (350 mL) was treated with 1,8-diazabicyclo[5.4.0]undec-7-ene (30.2 g, 198.4 mmol). The resulting mixture was stirred at room temperature. After one hour, the reaction mixture was treated with 2-cyclopenten-1-one (19.57 g, 238.4 mmol). After an additional 18 hours, the reaction mixture was added to a 1 N hydrochloric acid/sodium chloride solution. The resulting mixture was extracted with diethyl ether. The combined ether extracts were dried over magnesium sulfate, filtered, and concentrated in vacuo. The residue was purified using silica-gel chromatography, eluting with a linear gradient of 10% ethyl acetate/hexanes to 50% ethyl acetate/hexanes, to give 22.81 g (68%) of the title compound. Melting point: 36–38° C.

FDMS: m/z=168 (M+).

Analysis calculated for $C_9H_{12}O_3$: C, 64.27; H, 7.19. Found: C, 64.54; H, 7.11.

EXAMPLE 1

(1S*,2S*,4S*,5R*,6R*)-2-Amino-4-hydroxybicyclo[3.1.0]hexane-2,6-dicarboxylic Acid

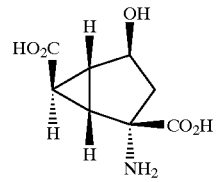

(a) (1S*,5R*,6S*)-Ethyl 2-oxobicyclo[3.1.0]hex-3-ene-6-carboxylate. Iodotrimethylsilane (50 g, 250 mmol) was added dropwise to a 0° C. solution of ethyl 2-oxobicyclo[3.1.0]-hexane-6-carboxylate (37 g, 220 mmol) and triethylamine (67 g, 660 mmol) in $CH_2Cl_2$ (1 L) and stirred for 1 hour. The reaction mixture was diluted with $Et_2O$, washed with saturated aqueous $NH_4Cl$, dried over $MgSO_4$ and concentrated to afford the silyl enolether (97%). To a 0° C. solution of the silyl enolether in $CH_3CN$ (300 mL) was added $Pd(OAc)_2$ in one portion. The resulting reaction mixture was allowed to warm to room temperature as it stirred overnight. The reaction mixture was diluted with $Et_2O$ filtered through celite and the product adsorbed onto 250 g $SiO_2$. The adsorbed silica was placed on top of a pad of silica, the product eluted with hexanes/EtOAc (4:1), and the resulting pink solid triturated with $Et_2O$ to afford 29.4 g (80%, 177 mmol) of the title compound as a white solid. mp=78–80° C. FDMS: M$^+$=166. Anal. calcd. for $C_9H_{10}O_3$: C, 65.05; H, 6.07. Found: C, 65.34; H, 6.10.

(a1) Alternative preparation of (1S*,5R*,6S*)-ethyl 2-oxobicyclo[3.1.0]-hex-3-ene-6-carboxylate. To a flame dried, 3 neck 3 L round bottom flask fitted with a $N_2$ inlet and reflux condenser was added a solution of the product from Preparation 2 (102 g, 424 mmol) in 425 mL anhydrous $CH_3CN$, allyl methyl carbonate (99 g, 848 mmol), and $Pd(OAc)_2$ (4.6 g, 20 mmol). The resulting reaction mixture was lowered into a heating bath prewarmed to 70° C. When the internal reaction temperature reached 40° C. a vigorous evolution of gas occurred and ceased after the reaction was complete 30 minutes later. The reaction mixture was diluted with EtOAC (2 L), filtered through $SiO_2$ (≈250 g), and concentrated under reduced pressure to yield 80 g of the crude product. Recrystallization from 10% EtOAc/hexanes afforded pure product, identical in every respect to that obtained in step (a).

(b) (1S*,3R*,4R*,5R*,6S*)-Ethyl 2-oxobicyclo[3.1.0] hex-3-ene-oxide-6-carboxylate. A 0° C. solution of the product of Step (a) (10.1 g, 60.8 mmol) in THF (300 mL) was treated sequentially with DBU (27.75 g, 182 mmol) then tert-butyl hydroperoxide. The resulting reaction mixture was stirred at 0° C. for 1 hour, diluted with $Et_2O$, and partitioned with 1N HCl. The product was extracted with $Et_2O$, dried over $MgSO_4$, and the resulting solid triturated in hexanes/EtOAc (9:1) to afford 9.83 g (89%, 54 mmol) of the title compound. mp=102–104° C. FDMS: $M^++1=182$. Anal. calcd. for $C_9H_{10}O_4$: C, 59.34; H, 5.53. Found: C, 59.24; H, 5.53.

(c) (1S*,4S*,5R*,6S*)-Ethyl 2-oxo-4-hydroxy-bicyclo-[3.1.0]hexane-6-carboxylate. To a stirred degassed suspension of N-acetyl-L-cysteine (25.64 g, 157 mmol), sodium borate·10 $H_2O$ (59.88 g, 157 mmol), and diphenyldiselenide (0.82 g, 2.62 mmol) in water/EtOH (1:1) (500 mL) was added the product of step (b) in THF (250 mL). Upon complete addition the reaction was stirred at room temperature overnight. The reaction mixture was diluted with $Et_2O$ and partitioned with $H_2O$. The product was extracted with $Et_2O$, washed with $H_2O$ then brine, and dried over $MgSO_4$. The product was purified by HPLC (hexanes/EtOAc) to afford 7.91 g (82%, 43 mmol) of the title compound. mp=60–62° C. FDMS: $M^+=184$. Anal. calcd. for $C_9H_{12}O_4$: C, 58.69; H, 6.57. Found: C, 58.70; H, 6.34.

(d) (1S*,2S*,4S*,5R*,6R*)-Ethyl 2-5'-spirohydantoin-4-hydroxybicyclo[3.1.0]-hexane-6-carboxylate. To a stirred solution of the product of step (c) (7.50 g, 40.7 mmol) in $EtOH/H_2O$ (1:1) (100 mL total volume) was added $NH_2CO_2NH_4$ 9.54 g, 122.2 mmol) then KCN (3.97 g, 61.1 mmol). Upon complete addition, the reaction mixture was warmed at 40° C. overnight. The reaction mixture was cooled to room temperature, acidified to pH=3 and the resulting precipitate removed by vacuum filtration to yield a 1:1 mixture of diastereomeric hydantoins. Recrystallization from EtOH (3X) yielded 0.79 g (3.1 mmol, 8%) of the desired diastereomer. mp=201–203° C. FDMS: $M^++1=255$. Anal. calcd. for $C_{11}H_{14}N_2O_5 \cdot 0.6\ H_2O$: C, 49.85; H, 5.78; N, 10.57. Found: C, 49.60; H, 5.68; N, 10.38.

(e) (1S*,2S*,4S*,5R*,6R*)-2-Amino-4-hydroxybicyclo-[3.1.0]hexane-2,6-dicarboxylic Acid. A solution of the product of step (d) (0.35 g, 1.38 mmol) in 1N NaOH (15 mL) was warmed under reflux overnight. The reaction mixture was cooled to room temperature and adjusted to pH=8. The resulting solids were filtered and discarded. The filtrate was then readjusted to pH=12 with 1N NaOH and applied to Bio-Rad AG1-X8 anion exchange resin (acetate form converted to hydroxide form). The product was eluted with 3N acetic acid to afford 0.25 g (90%, 1.2 mmol) of the title compound. mp=>275° C. FDMS: $M^++1=202$. Anal. calcd. for $C_8H_{11}NO_5 \cdot 0.25\ H_2O$: C, 46.72; H, 5.64; N, 6.81. Found: C, 46.68; H, 5.72; N, 6.59.

EXAMPLE 2

(1S*,2S*,5R*,6R*)-2-Amino-4-Oxobicyclo[3.1.0] Hexane-2,6-Dicarboxylic Acid

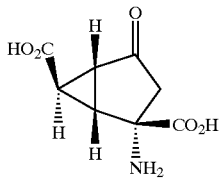

(a) (1S*,2S*,4S*,5R*,6R*)-Ethyl 2-(3'-benzyl-5'-spirohydantoin)-4-hydroxybicyclo[3.1.0]hexane-6-carboxylate. To a stirred solution of the product of Example 1, step (c) (14.5 g, 78.7 mmol) in $EtOH/H_2O$ (2:1) (150 mL total volume) was added $NH_2CO_2NH_4$ (18.42 g, 236 mmol) then KCN (7.68 g, 118 mmol). Upon complete addition, the reaction mixture was warmed at 40° C. for 2 days. The reaction mixture was concentrated in vacuo, partitioned with EtOAc/1N HCl, and brine. The mixture of hydantoins was extracted with EtOAc, dried over MgSO4, and concentrated. The crude hydantoins were reconstituted in DMF (50 mL) and stirred at room temperature as $NaHCO_3$ (16.85 g, 200 mmol) and then benzyl bromide (12.6 g, 73.5 mmol) were consecutively added. The reaction mixture was warmed at 100° C. overnight. The reaction mixture was diluted with EtOAc and partitioned with 0.5 N HCl. The hydantoins were extracted with EtOAC, washed with $H_2O$ then brine, dried over $MgSO_4$, and purified via HPLC (hexanes/EtOAc) to afford 5.14 g (19%, 14.9 mmol) of the title compound. FDMS: $M^+=344$.

Anal. calcd. for $C_{18}H_{20}N_2O_5$: C, 62.78; H, 5.85; N, 8.13. Found: C, 62.97; H, 5.97; N, 8.06.

(b) (1S*,2S*,5R*,6R*)-Ethyl 2-(3'-benzyl-5'-spirohydantoin)-4-oxo-bicyclo-[3.1.0]hexane-6-carboxylate. A 0° C. solution of the product of step (a) (1.03 g, 3.0 mmol) in acetone (20 mL) was treated in one portion with Jones Reagent (~2M, 7.5 mL-$CrO_1$, $H_2SO_4$, $H_2O$) and stirred at room temperature for 2 hours. 2-Propanol (2-mL) was added to quench the oxidant. The reaction mixture was then diluted with $Et_2O$, flashed through a pad of celite and $SiO_2$, and concentrated to yield 0.90 g (88%, 2.6 mmol) of the title compound. FDMS: $M^+=342$.

Anal. calcd. for $C_{18}H_{18}N_2O_5$: C, 63.15; H, 5.30; N, 8.18. Found: C, 62.87; H, 5.56; N, 8.26.

(c) Following the method of Example 1(e), the product of step (b) is hydrolyzed to afford the title compound.

EXAMPLE 3

(1S*,2R*,4R*, 5S*,6S*)-2-Aminobicyclo[3.1.0] Hexane-2,6-Dicarboxylic-4-Phosphonic Acid Monohydrochloride Monohydrate

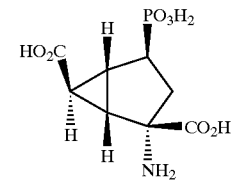

(a) (1S*,4R*,5S*,6S*)-Ethyl 2-oxo-4-(diethyl) phosphonobicyclo[3.1.0]hexane-6-carboxylate. A mixture of the product of Example 1(a) (1.6 g, 9.6 mmol), triethylphosphite (2.0 g, 12.0 mmol) in 4.2 g of phenol was heated at 100° C. overnight. The resulting reaction mixture was purified using HPLC (hexanes/EtOAc) to afford 2.7 g (92%, 8.9 mmol) of the title compound. mp=67–70° C. FDMS: $M^++1=305$.

Anal. calcd. for $C_{13}H_{21}O_6P$: C, 51.32; H, 6.96. Found: C, 51.11; H, 6.89.

(b) (1S*,2R*,4R*, 5S*,6S*)-Ethyl 2-aminoacetyl-2-cyano-4-(diethyl) phosphonobicyclo[3.1.0]-hexane-6-carboxylate. A mixture of KCN (3.2 g, 49 mmol), $NH_4Cl$ (2.6 g, 49 mmol) and $Al_2O_3$ (25 g) in $CH_3CN$ were sonicated under $N_2$ in a Branson 3200 ultrasonic bath for 1 hr. Then the product of step (a) (1.5 g, 4.9 mmol) was added and sonicated for 72 hrs at 45° C. The reaction mixture was filtered through Celite® and the filtrate was concentrated to dryness. The intermediate amino nitrile so obtained was dissolved in $CH_2Cl_2$, cooled to 0° C., and treated with acetyl chloride (0.5 g, 6.4 mmol) and N,N-diisopropylethylamine (0.8 g, 6.4 mmol). The reaction was allowed to proceed at ambient temperature for 1 h, then the mixture was partitioned between $CH_2Cl_2$ and $H_2O$. The organic phase was separated, dried ($MgSO_4$), filtered and concentrated under reduced pressure. The crude products were purified by chromatography (hexane/EtOAc). From this was obtained 1.0 g (55%) ethyl-2-aminoacetyl-2-cyano-4-diethylphosphonate bicyclo[3.1.0]hexane-6-carboxylate, (isomer A) and 0.10 g (5%) of ethyl-2-aminoacetyl-2-cyano-4-diethylphosphonatebicyclo[3.1.0]hexane-6-carboxylate (isomer B). (isomer A): mp=135–138° C. FDMS: $M^++1=373$.

Anal. calcd. for $C_{16}H_{25}N_2O_6P$: C, 51.61; H, 6.77; N, 7.52. Found: C, 51.89; H, 6.78; N, 7.75.

(c) (1S*,2R*,4R*, 5S*,6S*)-2-Aminobicyclo[3.1.0] hexane-2,6-dicarboxylic-4-phosphonic acid monohydrochloride monohydrate. The title compound was prepared by refluxing the product of step (b) (isomer A) (0.08 g, 0.2 mmol) in 30 mL of 6N HCl for 48 hours. The crude product was concentrated and purified using an anion exchange column eluted with 1N HCl. Collected 0.06 g (99%, 0.2 mmol) of the title compound. FDMS: $M^++1=266$.

Anal. calcd. for $C_8H_{12}NO_7P\cdot HCl\cdot H_2O$: C, 30.06; H, 4.73; N, 4.38. Found: C, 29.87; H, 4.36; N, 4.13.

EXAMPLE 4

(1S*,2S*,4S*, 5R*,6R*) 2-Amino-4-Methoxybicyclo[3.1.0]Hexane-2,6-Dicarboxylic Acid

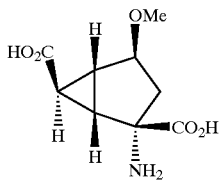

(a) (1S*,2S*,4S*, 5R*,6R*)-Diethyl 2-N-t-butyloxycarbonylamino-4-hydroxybicyclo[3.1.0]hexane-2,6-dicarboxylate. To a stirred solution of the product from Example 1(c) (23.9 g, 130 mmol) in EtOH/$H_2O$ (1:1) (500 mL total volume) was added $(NH_4)_2CO_3$ (30.4 g, 390 mmol) then KCN (12.7 g, 195 mmol). Upon complete addition, the reaction mixture was warmed at 40° C. until complete. The reaction mixture was cooled to 0° C., acidified to pH=1 with concentrated HCl and the mixture of diastereomeric 5'-spirohydantoins extracted with EtOAc. All organics were combined, washed with brine, dried over MgSO4 and concentrated under reduced pressure to afford a 1:1 mixture of crude hydantoins. The mixture of crude 5'-spirohydantoins (27.9 g, 110 mmol) was warmed under reflux in 2N NaOH (275 mL) for 5 days until the reaction was judged complete by TLC. The reaction mixture was cooled to 0° C., acidified to pH=1 with conc. HCl, and concentrated to dryness in vacuo. The resulting solids were reconstituted in 100% EtOH (500 mL), and chilled to 0° C. $SOCl_2$ (120 g, 1 mol) was then added dropwise to the reaction mixture at a rate to maintain reaction temperature at 10° C. Upon complete addition the reaction was warmed at reflux overnight. The reaction mixture was then concentrated in vacuo and reconstituted in a 1:1 mixture of saturated aqueous $NaHCO_1$:THF (500 mL) total volume. $Boc_2O$ (118 g, 550 mmol) was then added to the reaction mixture in one portion and stirred at room temperature overnight. The reaction mixture was then reduced in vacuo an the crude N-Boc diethylesters extracted with EtOAc. All the organic extracts were combined, washed with $H_2O$ then brine, dried over $K_2CO_1$, and concentrated to yield 120 g of crude product. The two diastereomers are isolated and purified via prep-HPLC (100% hexanes to 50% EtOAc/hexanes) to yield 10.12 g (26%, 28 mmol) of the desired product as a foam. FDMS: $M^++1=358$.

Anal. calcd. for $C_{17}H_{27}NO_7$: C, 57.13; H, 7.61; N, 3.92. Found: C, 56.84; H, 7.64; N, 3.96.

(b) (1S*,2S*,4S*, 5R*,6R*)-Diethyl 2-N-t-butyloxycarbonylamino-4-methoxybicyclo[3.1.0]hexane-2,6-dicarboxylate. To a 0° C. solution of the product of step (a) (0.50 g, 1.4 mmol) in THF (30 mL) was added NaH (0.07 g, 1.7 mmol) in one portion followed by dropwise addition of methyl iodide (0.21 g, 1.5 mmol). The resulting reaction mixture was allowed to warm to room temperature as it stirred overnight. The reaction was diluted with $H_2O$ and the product extracted with EtOAc. All organics were combined, washed with brine, dried over $K_2CO_1$, concentrated under reduced pressure and purified by PC-TLC (10% EtOAc/hexanes to 90% EtOAc/hexanes) to afford 0.12 g (0.32 mmol, 23%) of the desired product. FDMS: $M^++1=372$.

Anal. calcd. for $C_{18}H_{29}NO_7$: C, 58.21; H, 7.87; N, 3.77. Found: C, 58.69; H, 7.52; N, 4.85.

(c) (1S*,2S*,4S*, 5R*,6R*)-Diethyl 2-Amino-4-methoxybicyclo[3.1.0]-hexane-2,6-dicarboxylate. A 0° C. solution of the product from step (b) in EtOAc (25 mL) was purged with anhydrous HCl gas until the solution reached saturation.

The resulting reaction mixture was stirred at 0° C. for 1 hour and then concentrated to dryness under reduced pressure. The solids were dissolved in saturated $NaHCO_1$ (aq) and the product extracted with EtOAc. All organics were combined, washed with brine, dried over $K_2CO_1$, concentrated under reduced pressure and purified by PC-TLC (10% EtOAc/hexanes to 100% EtOAc) to afford 0.05 g (0.18 mmol, 61%) of the desired product. FDMS: $M^++1=271$. $^1H$ NMR ($CDCl_3$): δ 1.25 (t, J=7 Hz, 3H), 1.29 (t, J=7 Hz, 3H), 1.61 (t, J=3 Hz, 1H), 1.80–1.95 (br m 3H), 2.17–2.20 (m, 1H), 2.46–2.50 (m, 2H), 3.27 (s, 3H), 3.85–3.87 (m, 1H), 4.15 (q, J=7 Hz, 2H), 4.24 (q, J=7 Hz, 2H). $^{13}C$ NMR ($CDCl_3$): δ 13.96, 14.11, 20.82, 31.90, 33.96, 40.17, 56.00, 60.69, 61.26, 64.63, 82.14, 172.14, 174.85.

Anal. calcd. for $C_{13}H_{21}NO_5$: C, 57.55; H, 7.80; N, 5.16. Found: C, 56.04; H, 7.70; N, 5.81.

(d) (1S*,2S*,4S*, 5R*,6R*)-2-Amino-4-methoxybicyclo[3.1.0]-hexane-2,6-dicarboxylate. The product from step (c) (0.04 g, 0.11 mmol) was stirred in a 1:1 solution of 1N NaOH/THF (10 mL total volume) at room temperature overnight. The reaction mixture was acidified to pH=1 with 6N HCl and concentrated to dryness. The resulting solids were reconstituted in water at pH=2, applied to Dowex® 50X8-100 cation exchange resin, eluted with 10% pyridine/$H_2O$ to afford 0.012 g (37%, 0.06 mmol) of the desired product. mp=>275° C. FDMS: $M^++1=216$. $^1$NMR ($D_2O$/KOD): δ 1.08–1.14 (m, 2H), 1.74–2.07 (m 3H), 3.05 (s, 3H), 3.65–3.75 (m, 1H).

Anal. calcd. for $C_9H_{11}NO_5\cdot 0.2$ NaCl: C, 47.64; H, 5.78; N, 6.17. Found: C, 47.75; H, 5.74; N, 7.49.

EXAMPLE 5

(1S*,2S*, 5R*,6R*) 2-Amino-4-Oxobicyclo[3.1.0]
Hexane-2,6-Dicarboxylic Acid

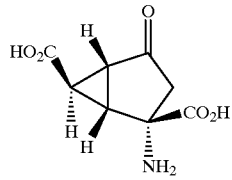

(a) (1S*,2S*, 5R*,6R*)-Diethyl 2-N-t-butyloxycarbonylamino-4-oxobicyclo[3.1.0]hexane-2,6-dicarboxylate. A solution of the product from Example 4(a) (0.50 g, 1.4 mmol) in $CH_2Cl_2$ (15 mL) was stirred at room temperature as pyridinium dichromate (1.60 g, 4.2 mmol) was added in one portion. The resulting reaction mixture was stirred at room temperature overnight. The reaction was diluted with EtOAc and filtered through celite to remove chromium by-products. The filtrate was concentrated in vacuo and purified via PC-TLC (10% EtOAc/hexanes to 20% EtOAc/hexanes) to yield 0.49 g (1.38 mmol, 98%) of a white foam. FDMS: $M^+ + 1 = 356$.

Anal. calcd. for $C_{17}H_{25}NO_7$: C, 57.46; H, 7.09; N, 3.94. Found: C, 57.60; H, 7.14; N, 4.03.

(b) (1S*,2S*, 5R*,6R*)-2-Amino-4-oxobicyclo[3.1.0]hexane-2,6-dicarboxylic acid. A 0° C. solution of the product from step (a) (0.37 g, 1.04 mmol) in EtOAc (30 mL) was purged with anhydrous HCl gas until saturation occurred. The resulting reaction mixture was stirred at 0° C. for 1 hour then concentrated to dryness in vacuo. The resulting solids were reconstituted in 10 mL 1N NaOH and stirred overnight. The reaction mixture was adjusted to pH=2 with 6N HCl, applied to Dowex® 50X8-100 cation exchange resin, an the product eluted with 10% Pyridine/$H_2O$. The product was obtained from a recrystallization from $H_2O$ to afford 0.06 g (31%, 0.30 mmol) of the desired product. mp=dec>210° C. FDMS: $M^+ + 1 = 200$.

Anal. calcd. for $C_8H_9NO_5$: C, 48.25; H, 4.55; N, 7.03. Found: C, 48.19; H, 4.46; N, 7.16.

EXAMPLE 6

(1S*,2S*, 5R*,6R*) 2-Amino-4-[Anti]-Hydroximinobicyclo[3.1.0]Hexane-2,6-Dicarboxylic Acid and (1S*,2S*, 5R*,6R*) 2-Amino-4-[syn]-Hydroximinobicyclo[3.1.0]Hexane-2,6-Dicarboxylic Acid

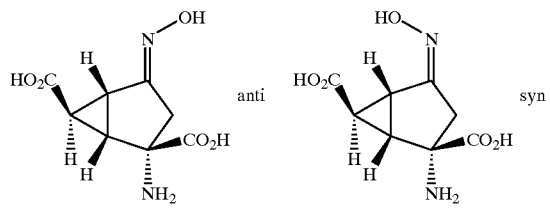

(a) (1S*,2S*, 5R*,6R*)-Diethyl 2-Amino-4-oxobicyclo[3.1.0]-hexane-2,6-dicarboxylate. A 0° C. solution of the product from Example 5(a) (0.37 g, 1.04 mmol) in EtOAc (30 mL) was purged with anhydrous HCl gas until saturation occurred. The resulting reaction mixture was stirred at 0° C. for 1 hour. The reaction mixture was diluted with saturated aqueous $NaHCO_1$ and the product extracted with EtOAc. All organics were combined, washed with brine, dried over $K_2CO_1$ and concentrated in vacuo to yield the desired intermediate (0.36 g, 1.4 mmol, 100%). FDMS: $M^+ + 1 = 256$.

Anal. calcd. for $C_{12}H_{17}NO_5$.0.2 $H_2O$: C, 55.68; H, 6.78; N, 5.41. Found: C, 55.47; H, 5.91; N, 5.24.

(b) (1S*,2S*,4R*, 6R*)-Diethyl 2-Amino-4-hydroximinobicyclo[3.1.0]hexane-2,6-dicarboxylate. Hydroxylamine hydrochloride (0.15 g, 2.1 mmol) was added to a room temperature solution of the product from step (a) (0.36 g, 1.4 mmol) and NaOAc (0.23 g, 2.8 mmol) in a 3:1 mixture of EtOH/$H_2O$ (20 mL total volume) and heated at 80° C. for 1 hour. Aqueous $NaHCO_3$ was added to the reaction mixture, the product extracted with EtOAc, washed with brine, dried over $K_2CO_3$ and concentrated in vacuo to afford a 2:1 mixture of the E and Z isomers. Purification by PC-TLC (10% EtOAc/hexanes to 67% EtOAc/hexanes) afforded clean products. anti-isomer: 0.18 g (0.67 mmol, 56%). FDMS: $M^+ + 1 = 271$.

Anal. calcd. for $C_{12}H_{18}N_2O_5$.0.35 $CH_2Cl_2$: C, 49.44; H, 6.28; N, 9.34. Found: C, 49.62; H, 5.89; N, 9.39. syn-isomer: 0.09 g (0.33 mmol, 28%). mp=135–137° C. FDMS: $M^+ + 1 = 271$.

Anal. calcd. For $C_{12}H_{18}N_2O_5$.0.1 hexanes: C, 54.26; H, 7.01; N, 10.04. Found: C, 54.03; H, 6.71; N, 10.14.

(c) (1S*,2S*, 5R*,6R*)-2-Amino-4-[anti]-hydroximinobicyclo[3.1.0]hexane-2,6-dicarboxylic acid. A solution of the anti-oxime from step (b) (0.13 g, 0.48 mmol) was stirred at room temperature in a 1:1 mixture of 1N NaCH:THF (20 mL total volume) for 4 days. The reaction mixture was then diluted with $H_2O$ and the product washed with EtOAc (3X) to remove organic impurities. The aqueous layer was adjusted to pH=10 with 1N HCl and concentrated in vacuo. The solids were reconstituted in $H_2O$ and purified by anion-exchange chromatography (Bio-Rad® AG1-X8: elution with 3N AcOH). Recrystallization from $H_2O$/2-propanol (1:1) afforded 0.07 g (0.33 mmol, 68%) of the product. mp=dec>260° C. FDMS: $M^+ + 1 = 215$.

Anal. calcd. for $C_8H_{10}N_2O_5$.0.15 $H_2O$: C, 44.30; H, 4.79; N, 12.91. Found: C, 44.53; H, 4.48; N, 12.51.

(d) (1S*,2S*, 5R*,6R*)-2-Amino-4-[syn]-hydroximinobicyclo[3.1.0]hexane-2,6-dicarboxylic acid. Utilizing 0.085 g (0.31 mmol) of the syn-oxime product from step (b), the reaction conditions, work-up and isolation were identical to those in step (c). Yield 0.04 g (0.19 mmol, 60%). mp=dec>250° C. FDMS: $M^+ + 1 = 215$.

Anal. calcd. for $C_8H_{10}N_2O_5$.0.15 NaCl: C, 43.10; H, 4.52; N, 12.57. Found: C, 43.46; H, 4.74; N, 11.75.

EXAMPLE 7

(1S*,2R*,4S*, 5S*,6S*)-2-Amino-4-Fluorobicyclo [3.1.0]hexane-2,6-Dicarboxylic Acid

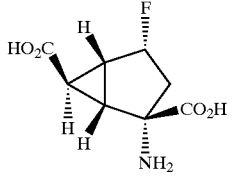

(a) (1S*,2R*,4S*, 5S*,6S*)-Diethyl 2-N-t-butyloxycarbonylamino-4-fluorobicyclo[3.1.0]hexane-2,6-dicarboxylate. To a 0° C. solution of the product from Example 4(a) (0.50 g, 1.40 mmol) in $CH_2Cl_2$ (25 mL) was added diethylaminosulfur trifluoride (DAST) in one portion. The resulting reaction mixture was allowed to warm to room temperature as it stirred overnight. The reaction was diluted with 10% aqueous $NaHCO_3$ and the product extracted with EtOAc. All organics were combined, washed with brine, dried over $K_2CO_3$ and purified via PC-TLC (10% EtOAc/hexanes to 20% EtOAc) to afford 0.38 g (1.06 mmol, 74%) of the desired product as a clear colorless oil. FDMS: $M^++1=360$.

Anal. calcd. for $C_{17}H_{26}NO_6$: C, 56.81; H, 7.29; N, 3.90. Found: C, 56.79; H, 7.42; N, 4.11.

(b) (1S*,2R*,4S*,5S*,6S*)-Diethyl 2-Amino-4-fluorobicyclo[3.1.0]hexane-2,6-dicarboxylate. A 0° C. solution of the product from step (a) (0.33 g, 0.92 mmol) in EtOAc (30 mL) was purged with anhydrous HCl gas until saturation occurred.

The resulting reaction mixture was stirred at 0° C. for 1 hour. The reaction mixture was diluted with saturated aqueous $NaHCO_3$ and the product extracted with EtOAc. All organics were combined, washed with brine, dried over $K_2CO_3$ and concentrated in vacuo to afford 0.23 g (0.89 mmol, 96%) of the desired product. FDMS: $M^++1=260$.

Anal. calcd. for $C_{12}H_{17}FNO_4$: C, 55.59; H, 7.00; N, 5.40. Found: C, 55.56; H, 6.79; N, 5.21.

(c) (1S*,2R*,4S*,5S*,6S*)-2-Amino-4-fluorobicyclo [3.1.0]hexane-2,6-dicarboxylic acid. A solution of the product from step (b) (0.12 g, 0.46 mmol) in a 1:1 mixture of 1N NaOH:THF- (20 mL total volume) was stirred at room temperature overnight. The reaction mixture was then adjusted to pH=12 with 6N HCl and purified via anion exchange chromatography (Bio-Rad® AG1-X8 ion exchange resin. 3N acetic acid as eluent. Recrystallization from $H_2O$/2-propanol (1:1) afforded 0.04 g (0.20 mmol, 49%) of the desired product. mp=dec>260° C. FDMS: $M^++1=204$.

Anal. calcd. for $C_8H_{10}FNO_4 \cdot 0.45$ NaCl: C, 41.87; H, 4.39; N, 6.10. Found: C, 41.91; H, 4.00; N, 5.76.

EXAMPLE 8

(1S*,2S*,4R*,5R*,6S*) 2,4-Diaminobicyclo[3.1.0] Hexane-2,6-Dicarboxylate Acid

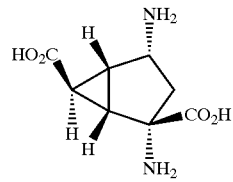

(a) (1S*,2S*,4S*,5R*,6R*)-Diethyl 2-N-t-butyloxycarbonylamino-4-(p-toluenesulfonyloxy)bicyclo [3.1.0]hexane-2,6-dicarboxylate. p-Toluenesulfonyl chloride (5.3 g, 28 mmol) was added to a solution of the product of Example 4(a) (5.0 g, 14 mmol) in pyridine (25 mL) and the resulting reaction mixture stirred at room temperature overnight. The reaction mixture was diluted with EtOAc (100 mL) and washed with saturated aqueous $CuSO_4$ to remove the pyridine. The organics were washed with brine, dried over $MgSO_4$ and concentrated under reduced pressure to afford the crude product which was purified by $SiO_2$ chromatography (HPLC: 10% EtOAc/hexanes to 50% EtOAc/hexanes) to obtain 6.55 g (91%, 12.8 mmol) of the desired product as a white foam. FDMS: $M^++1=512$.

Anal. calcd. for $C_{24}H_{11}NO_9S$: C, 56.35; H, 6.50; N, 2.74. Found: C, 56.48; H, 6.44; N, 2.60.

(b) (1S*,2S*,4R*,5R*,6S*)-Diethyl 2-N-t-butyloxycarbonylamino-4-azidobicyclo[3.1.0]hexane-2,6-dicarboxylate. A solution of the product from step (a) (6.35 g, 12.4 mmol) and $NaN_1$ (2.42 g, 37.2 mmol) in DMSO (15 mL) was warmed at 35° C. for 3 days. The reaction mixture was diluted with $H_2O$ and the product extracted with EtOAc. All organics were combined, washed with brine, dried over $MgSO_4$, and concentrated under reduced pressure to yield the crude azide which was purified by vacuum filtration through $SiO_2$ (20% EtOAc/hexanes to 50% EtOAc/hexanes) to afford 4.68 g (98%, 12.2 mmol) of the desired product as a waxy solid. FDMS: $M^++1=512$.

Anal. calcd. for $C_{17}H_{26}N_4O_6 \cdot 0.1$ hexanes: C, 54.06; H, 7.06; N, 14.33. Found: C, 53.94; H, 6.88; N, 14.30.

(c) (1S*,2S*,4S*,5R*,6S*)-Diethyl 2-N-t-butyloxycarbonyl-4-aminobicyclo[3.1.0]hexane-2,6-dicarboxylate. Triphenylphosphine (2.90 g, 11 mmol) was added in one portion to a solution of the product of step (b) (3.5 g, 9.2 mmol) in THF/$H_2O$ (5:1) and stirred at room temperature overnight. The reaction mixture was diluted with EtOAc and washed with 0.5N NaOH (3X). The organics were combined, washed with $H_2O$ then brine, dried over $K_2CO_3$, concentrated under reduced pressure and purified by $SiO_2$ chromatography (HPLC: $SiO_2$ (10% EtOAc/hexanes to 50% EtOAc/hexanes) to afford 2.03 g (62%, 5.7 mmol) of the desired product as a foam. FDMS: $M^++1=357$.

Anal. calcd. for $C_{17}H_{28}N_2O_6$: C, 57.30; H, 7.92; N, 7.86. Found: C, 57.02; H, 7.73; N, 7.72.

(d) (1S*,2S*,4R*,5R*,6S*) 2,4-Diaminobicyclo[3.1.0] hexane-2,6-dicarboxylate acid. The product from step (c) was warmed under reflux in 1N HCl overnight. The reaction mixture was adjusted to pH=2 with 1N NaOH and purified by cation exchange chromatography (Dowex® 50X8-100: 10% Pyridine/$H_2O$). The resulting product was recrystallized from 2-propanol/$H_2O$ (1:1) to yield 0.09 g (45%, 0.45 mmol) of the desired product as a white solid. mp=>275° C. FDMS: $M^++1=201$.

EXAMPLE 9

(1S*,2S*,4R*,5R*,6S*) 2-Amino-4-Azidobicyclo[3.1.0]Hexane-2,6-Dicarboxylate Acid

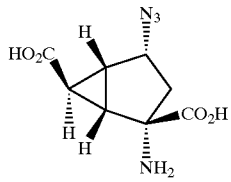

A solution of the product from Example 8(b) (0.25 g, 0.65 mmol), in EtOAc (30 mL) was chilled to 0° C. and purged with anhydrous HCl gas until the solution reached saturation. The reaction mixture was stirred at 0° C. for two hours, concentrated to dryness, and the resulting solid stirred in a 1:1 mixture of 1N NaOH:THF (20 mL total volume) at room temperature overnight. The THF was removed under reduced pressure, the aqueous mixture adjusted to pH=12 with 1N HCl, and purified by anion exchange chromatography (Bio-Rad® AG1-X8: acetate form converted to hydroxide form, elute with 3N acetic acid) to yield 0.10 g (0.44 mmol, 68%) of the desired product. mp=dec>270° C. FDMS: $M^++1=227$.

Anal. calcd. for $C_8H_{10}N_4O_4$·0.2 AcOH: C, 42.36; H, 4.57; N, 23.52. Found: C, 41.96; H, 4.54; N, 23.55.

EXAMPLE 10

(1S*,2S*,4R*,5R*,6S*) 2-Amino-4-Acetamidobicyclo[3.1.0]Hexane-2,6-Dicarboxylic Acid

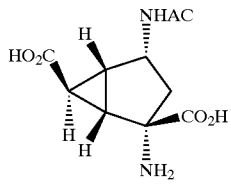

(a) (1S*,2S*,4R*,5R*,6S*)-Diethyl 2-N-t-butyloxycarbonylamino-4-acetamidobicyclo[3.1.0]hexane-2,6-dicarboxylate. Acetyl chloride (0.09 g, 1.1 mmol) was added by dropwise addition to a 0° C. solution of the product from Example 8(c) (0.35 g, 1.0 mmol) and triethylamine (0.20 g, 2.0 mmol) in $CH_2Cl_2$ (20 mL), and the resulting reaction mixture allowed to warm to room temperature as it stirred overnight. The reaction mixture was diluted with $Et_2O$, washed with aqueous $NaHSO_4$ then brine, dried over $MgSO_4$ and concentrated in vacuo to yield the crude acetamide which was purified by PC-TLC (10% EtOAc/hexanes to 67% EtOAc/hexanes) to afford 0.35 g (88%, 0.88 mmol) of the desired product as a white solid. mp=dec 85–95° C. FDMS: $M^++1=399$.

Anal. calcd. for $C_{19}H_{30}N_2O_7$: C, 57.27; H, 7.58; N, 7.03. Found: C, 57.41; H, 7.28; N, 6.94.

(b) (1S*,2S*,4R*,5R*,6S*)-2-Amino-4-acetamidobicyclo[3.1.0]hexane-2,6-dicarboxylic acid. A solution of the product from step (a) (0.30 g, 0.75 mmol), in EtOAc (30 mL) was chilled to 0° C. and purged with anhydrous HCl gas until the solution reached saturation. The reaction mixture was stirred at 0° C. for two hours, concentrated to dryness, and the resulting solid stirred in a 1:1 mixture of 1N NaOH:THF (20 mL total volume) at room temperature overnight. The THF was removed under reduced pressure, the aqueous mixture adjusted to pH=2 with 1N HCl, and purified by cation exchange chromatography (Dowex® 50X8-100, elute with 10% pyridine/$H_2O$). Recrystallization from $H_2O$/2-propanol (1:1) afforded 0.09 g (0.37 mmol, 50%) of the desired product. mp=>275° C. FDMS: $M^++1=243$.

Anal. calcd. for $C_{10}H_{14}N_2O_5$·0.3 NaCl: C, 46.24; H, 5.43; N, 10.78. Found: C, 45.93; H, 5.50; N, 10.88.

EXAMPLE 11

(1S*,2S*,4R*,5R*,6S*) 2-Amino-4-Benzoylaminobicyclo[3.1.0]Hexane-2,6-Dicarboxylic Acid

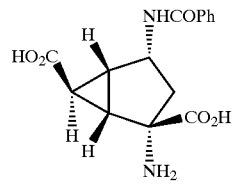

(a) (1S*,2S*,4R*,5R*,6S*)-Diethyl 2-N-t-butyloxycarbonylamino-4-benzoylaminobicyclo[3.1.0]hexane-2,6-dicarboxylate. Benzoyl chloride (0.16 g, 1.1 mmol) was added by dropwise addition to a 0° C. solution of the product from Example 8(c) (0.35 g, 1.0 mmol) and triethylamine (0.20 g, 2.0 mmol) in $CH_2Cl_2$ (20 mL), and the resulting reaction mixture allowed to warm to room temperature as it stirred overnight. The reaction mixture was diluted with $Et_2O$, washed with aqueous $NaHSO_4$ then brine, dried over $MgSO_4$ and concentrated in vacuo to yield the crude amide which was purified by PC-TLC (10% EtOAc/hexanes to 67% EtOAc/hexanes) to afford 0.31 g (67%, 0.67 mmol) of the desired product as a white foam. FDMS: $M^++1=461$.

Anal. calcd. for $C_{24}H_{32}N_2O_7$: C, 62.59; H, 7.00; N, 6.08. Found: C, 62.75; H, 6.70; N, 5.99.

(b) (1S*,2S*,4R*,5R*,6S*)-2-Amino-4-benzoylaminobicyclo[3.1.0]hexane-2,6-dicarboxylic acid. A solution of the product from step (a) (0.30 g, 0.75 mmol), in EtOAc (30 mL) was chilled to 0° C. and purged with anhydrous HCl gas until the solution reached saturation. The reaction mixture was stirred at 0° C. for two hours, concentrated to dryness, and the resulting solid stirred in a 1:1 mixture of 1N NaOH:THF (20 mL total volume) at room temperature overnight. The THF was removed under reduced pressure, the aqueous mixture adjusted to pH=2 with 1N HCl, and purified by cation exchange chromatography (Dowex® 50X8-100, elute with 10% pyridine/$H_2O$). Recrystallization from $H_2O$/2-propanol (1:1) afforded 0.095 g (0.31 mmol, 58%) of the desired product. mp=dec>275° C. FDMS: $M^++1=305$.

Anal. calcd. for $C_{15}H_{16}N_2O_5$·0.3 2-propanol: C, 59.25; H, 5.75; N, 8.69. Found: C, 59.50; H, 5.65; N, 8.32.

EXAMPLE 12

(1S*,2S*,4R*,5R*,6S*) 2-Amino-4-(Methanesulfonylamino)Bicyclo[3.1.0]Hexane-2,6-Dicarboxylic Acid

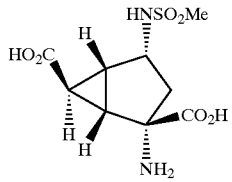

(a) (1S*,2S*,4R*,5R*,6S*)-Diethyl 2-N-t-butyloxycarbonylamino-4-(methanesulfonylamino)bicyclo [3.1.0]hexane-2,6-dicarboxylate. Methanesulfonyl chloride (0.13 g, 1.1 mmol) was added by dropwise addition to a 0° C. solution of the product from Example 8(c) (0.35 g, 1.0 mmol) and triethylamine (0.21 g, 2.0 mmol) in $CH_2Cl_2$ (25 mL), and the resulting reaction mixture stirred at 0° C. for 1 hour. The reaction mixture was diluted with EtOAc, washed with aqueous $NaHSO_4$ then brine, dried over $MgSO_4$ and concentrated in vacuo to yield the crude methylsulfonamide which was purified by PC-TLC 910% EtOAc/hexanes to 67% EtOAc/hexanes) to afford 0.44 g (99%, 1.0 mmol) of the desired product as a white foam. FDMS: $M^++1=435$.

Anal. calcd. for $C_{18}H_{30}N_2O_8S$: C, 49.76; H, 6.96; N, 6.45; S, 7.38. Found: C, 50.04; H, 6.68; N, 6.21; S, 7.38.

(b) (1S*,2S*,4R*,5R*,6S*)-2-Amino-4-(methanesulfonylamino)bicyclo[3.1.0]hexane-2,6-dicarboxylic acid. A solution of the product from stap (a) (0.40 g, 0.92 mmol), in EtOAc (30 mL) was chilled to 0° C. and purged with anhydrous HCl gas until the solution reached saturation. The reaction mixture was stirred at 0° C. for two hours, concentrated to dryness, and the resulting solid stirred in a 1:1 mixture of 1N NaOH:THF (20 mL total volume) at room temperature overnight. The THF was removed under reduced pressure, the aqueous mixture adjusted to pH=2 with 1N HCl, and purified by cation exchange chromatography (Dowex® 50X8-100, elute with 10% pyridine/$H_2O$). Recrystallization from $H_2O$/2-propanol (1:1) afforded 0.13 g (0.46 mmol, 50%) of the desired product. mp=>275° C. FDMS: $M^++1=279$.

Anal. calcd. for $C_9H_{14}N_2O_6S$: C, 38.84; H, 5.07; N, 10.07. Found: C, 39.01; H, 5.21; N, 10.07.

EXAMPLE 13

(1S*,2S*,4R*,5R*,6S*) 2-Amino-4-(Methylaminocarbonylamino)-Bicyclo [3.1.0]hexane-2,6-Dicarboxylic Acid

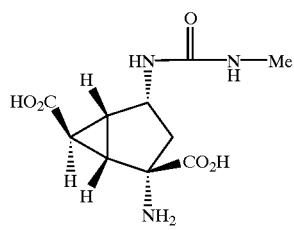

(a) 1S*,2S*,4R*,6S*)-Diethyl 2N-t-butyloxycarbonyl-amino-4-(methylaminocarbonylamino) bicyclo[3.1.0] hexane-2,6-dicarboxylate. Methyl isocyanate (2.07 g, 1.2 mmol) was added by dropwise addition to a 0° C. solution of the product from Example 8(c) (0.35 g, 1.0 mmol) in $CH_2Cl_2$ (25 mL), and the resulting reaction mixture allowed to warm to room temperature as it stirred overnight. The reaction mixture was diluted with EtOAc, washed with aqueous $NaHSO_4$ then brine, dried over $MgSO_4$ and concentrated in vacuo to yield the crude methyl urea which was purified by PC-TLC (10% EtOAc/hexanes to 50% EtOAc/hexanes) to afford 0.35 g (85%, 0.85 mmol) of the desired product as a white foam. FDMS: $M^{30}+1=414$. Anal. calcd. for $C\_H\_N_3O_7.0.5\ H_2O$: C, 54.01; H, 7.63; N, 9.95;. Found: C, 53.81; H, 7.52; N, 10.64.

(b) (2S*,2S*,4R*,6R*,6S*)-2-Amino-4-(methylaminocarbonyl-amino)bicyclo [3.1.0]hexane-2,6-dicarboxylic acid. A solution of the product from step (a) (0.30 g, 0.72 mmol), in EtOAc (30 mL) was chilled to 0° C. and purged with anhydrous HCl gas until the solution reached saturation. The reaction mixture was stirred at 0° C. for one hour, concentrated to dryness, and the resulting solid stirred in a 1:1 mixture of 1N NaOH:THF (20 mL total volume) at room temperature overnight. The THF was removed under reduced pressure, the aqueous mixture adjusted to pH=2 with 1N HCl, and purified by cation exchange chromatography (Dowex® 50×8-100, elute with 10% pyridine/$H_2O$). Recrystallization from $H_2O$/2-propanol (1:1) afforded 0.12 g (0.46 mmol, 64%) of the desired product. mp=>275° C. FDMS: $M^++1=258$. Anal. calcd. for $C_{10}H_{15}N_3O_5.0.1\ H_2$): C, 46.37; H, 5.91; N, 16.22. Found: C, 46.03; H, 6.01; N, 16.12.

EXAMPLE 14

(1S*,2S*,4R*,5R*,6S*) 2-Amino-4-(N,N-Dicyclopropylmethylamino)bicyclo[3.1.0]hexane-2,6-Dicarboxylic Acid

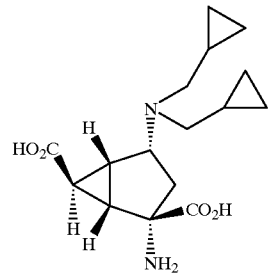

(a) (1S*,2S*,4R*,5R*,6S*)-Diethyl 2-N-t-butyloxycarbonyl-amino-4-(N,N-dicyclopropylmethylamino) bicyclo[3.1.0]hexane-2,6-dicarboxylate. Cyclopropylmethyl bromide (0.27 g, 2.0 mmol) was added by dropwise addition to a room temperature solution of the product from Example 8(c) (0.32 g, 0.90 mmol) and triethylamine (0.30 g, 3.0 mmol) in $CH_3CN$ (25 mL), and the resulting reaction mixture stirred overnight. The reaction mixture was concentrated in vacuo and purified by PC-TLC (10% EtOAc/hexanes to 67% EtOAc/hexanes) to afford 0.33 g (78%, 0.70 mmol) of the desired product as a light yellow oil. FDMS: $M^++1=465$. Anal. calcd. for $C_{25}H_{40}N_2O_6$: C, 64.63; H, 8.68; N, 6.03. Found: C, 64.38; H, 8.60; N, 5.93.

(b) (1S*,2S*,4R*,5R*,6S*)-2-Amino-4-(N,N-dicyclopropyl-methylamino)bicyclo[3.1.0]hexane-2,6-dicarboxylic acid. A solution of the product from step (a) (0.28 g, 0.61 mmol), in EtOAc (30 mL) was chilled to 0° C and purged with anhydrous HCl gas until the solution reached saturation. The reaction mixture was stirred at 0° C. for four hours, concentrated to dryness, and the resulting solid stirred in a 1:1 mixture of 1N NaOH:THF (20 mL total volume) at room temperature overnight. The THF was removed under reduced pressure, the aqueous mixture adjusted to pH=2 with 1N HCl, and purified by cation exchange chromatography (Dowex® 50×8–100, elute with 10% pyridine/$H_2O$. Recrystallization from $H_2O$/propanol (1:1) afforded 0.15 g (0.49 mmol, 80%) of the desired product. mp=dec>270° C. FDMS: $M^+ \div 1$=309. Anal. calcd. for $C_{16}H_{24}N_2O_4 \cdot 0.6 H_2O$: C, 60.21; H, 7.96; N, 8.78. Found: C, 59.92; H, 7.99; N, 8.93.

EXAMPLE 15

(1S*,2S*,5R*,6S*)-2-Amino-4-Z-Carboxymethylenebicyclo[3.1.0]Hexane-2,6-Dicarboxylic Acid (1S*,2S*,5R*,6S*)-2-Amino-4-E-Carboxymethylenebicyclo[3.1.0]Hexane-2.6-Dicarboxylic Acid

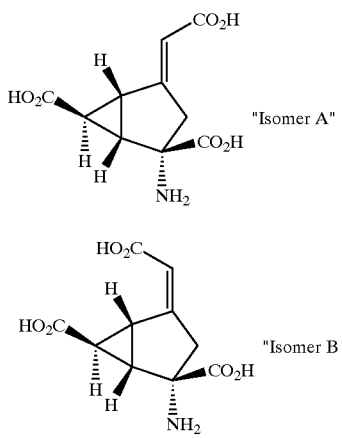

(a) (1S*,2S*,4R*,6S*)-Diethyl-2-(N-tert-butyloxycarbonyl)-amino-4-(benzyloxycarbonyl) methylene bicyclo[3.1.0]hexane-2,6-dicarboxylate, Isomers A and B. The sodium salt of benzyl diethylphosphonoacetate was prepared by the addition of sodium bis (trimethylsilyl)-amide (4.2 mmol) to an anhydrous toulene solution of benzyl diethylphosphonoacetate (1.2 g, 4.2 mmol) at 0° C. The sodium salt was rapidly added to a anhydrous toluene solution of the product of Example 5(a) (1.0 g, 2.8 mmol) at 0° C. and stirred for 15 minutes. The reaction was allowed to warm to room temperature and stir until it was determined to be complete by TLC. 1N HCl was added and the reaction mixture was extracted using ethyl acetate. The combined organic layers were washed with aqueous NaCl and dried with $MgSO_4$. The organics were concentrated and the crude product purified using HPLC (EtOAc/hexanes) to afford 1.3 g (94%) of a mixture of two isomers. FDMS: $M^+-1$=486. Anal. calcd. for $C_{26}H_{33}N_1O_8$: C, 64.05; H, 6.82; N, 2.87. Found: C, 64.04; H, 6.87; N, 2.96.

(b) (2S*,2S*,5R*,6S*)-Diethyl-2-amino-4-E-(benzyloxycarbonyl) methylenebicyclo[3.1.0]hexane-2,6-dicarboxylate, Isomer A and (1S*,2S*,4R*,6S*)-Diethyl-2-amino-4-Z-(benzyloxycarbonyl) methylenebicyclo[3.1.0] hexane-2,6-dicarboxylate, Isomer B. Anhydrous HCl (g) was bubbled into a EtOAc solution of the product of step (a) (0.4 g, 0.82 mmol) at 0° C. The reaction was allowed to warm to room temperature and stir until judged complete by TLC. The organics were partitioned over aqueous $NaHCO_3$, dried with $K_2CO_3$, and concentrated under vacuum. Purification by HPLC (EtOAc/hexanes) afforded 0.154 g (48%) isomer A and 0.13 g (41%) isomer B. Isomer A: FDMS: $M^++1$=388. Anal. calcd. for $C_{21}H_{25}N_1)_6$: C, 65.10; H, 6.50; N,3.62. Found: C, 64.91; H, 6.40; N, 3.83. Isomer B: FDMS: $M^+\div 1$=388. Anal. calcd. for $C_{21}H_{25}N_1O_6$+0.5 eq. $CH_2Cl_2$: C, 60.07; H, 6.10; N, 3.26. Found: C, 60.33; H, 6.05; N, 3.43.

(c) (1S*,2S*,5R*,6S*)-2-Amino-4-E-carboxymethylenebicyclo-[3.1.0]hexane-2,6-dicarboxylic acid. The product of step (b), Isomer A (0.134 g, 0.35 mmol), was stirred in 5 mL of 2N NaOH and 2 mL of THF for 5 hours. The reaction was adjusted to a pH=7 with 1N HCl and concentrated to dryness. The resulting solid was reconstituted in water at a pH=10 and applied to an anion exchange resin (Bio-Rad® AG1–X8, eluted with 2N acetic acid) to afford 0.038 g (45%) of the desired product. FDMS: $M^+\div 1$= 242. Anal. calcd. for $C_{10}H_{11}NO_6$+0.14 eq. NaCL: C, 48.16; H, 4.44; N, 5.62. Found: C, 48.15; H, 4.29; N, 5.36.

(d) (1S*,2S*,5R*,6S*)-2-Amino-4-Z-carboxymethylenebicyclo-[3.1.0]hexane-2,6-dicarboxylic acid. The product of step (b), Isomer B (0.107 g, 0.28 mmol), was stirred in 5 mL of 2N NaOH and 2mL of THF for 5 hours. The reaction was adjusted to a pH=7 with 1N HCl and concentrated to dryness. The resulting solid was reconstituted in water at a pH=10 and applied to an anion exchange resin (Bio-Rad® AG1–X8, eluted with 2N acetic acid) to afford 0.050 g (75%) of the desired product. FDMS: $M^++1$=242. Anal. calcd. for $C_{10}H_{11}NO_6$+1.0 eq. $H_2O$: C, 46.34; H, 5.06; N, 5.40. Found: C, 46.43; H, 5.04; N, 5.45.

EXAMPLE 16

(1S*,2S*,5R*,6S*)-2-Amino-4-Methylenebicyclo [3.1.0]Hexane-2,6-Dicarboxylic Acid

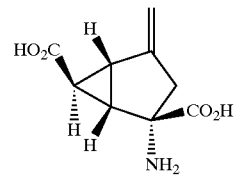

(a) (1S*,2S*,5R*,6S*)-Diethyl-2-(N-tert-butyloxycarbonyl)-amino-4-methylenebicyclo[3.1.0] hexane-2,6-dicarboxate. Sodium bis (trimethylsilyl) amide (4.2 mmol) was added to a slurry of methyltriphenylphosphonium bromide (1.5 g, 4.2 mmol) in anhydrous THF at 0° C. A solution of the product of Example 5(a) (0.75 g, 2.1 mmol) in anhydrous THF was added to the reaction vessel and stirred for overnight at 0° C. 1N HCl was added and the reaction mixture was extracted using ethyl acetate. The combined organic layers were washed with aqueous NaCl and dried with $MgSO_4$. The organics were concentrated and the crude product was purified using HPLC (EtOAc/ Hexanes) to afford 0.52 g (70%) of the desired product. FDMS: $M_+ \div 1$=354.

(b) (1S*,2S*,5R*,6S*)-2-Amino-4-methylenebicyclo [3.1.0]-hexane-2,6-dicarboxylic acid. The product of step (a) (0.36 g, 1.0 mmol) was stirred in 1 ml of TFA for 1 hour, concentrated and dissolved in 5 mL of THF. The reaction was adjusted to pH=13–14 with 1N NaOH and stirred for 2 hours. The reaction mixture was concentrated and adjusted to pH=10 with 1N HCl. The resulting material was applied to an anion exchange resin (Bio-Rad® AG1-X8, eluted with 1N acetic acid) to afford 0.061 g (31%) of the desired product. FDMS: M$^+$+1=198. Anal. calcd. for $C_9H_{11}NO_4$+ 0.25 eq. of $H_2O$: C, 53.60; H, 5.75; N, 6.94. Found: C, 53.65; H, 5.64; N, 6.85.

EXAMPLE 17

(1S*,2S*,5R*,6S*)-2-Amino-4-(Z)-(Diethylphosphonomethylene)-Bicyclo[3.1.0]Hexane-2,6-Dicarboxylic Acid
(1S*,2S*,5R*,6S*)-2-Amino-4-(E)-Diethylphosphonomethylene)-Bicyclo[3.1.0]hexane-2,6-Dicarboxylic Acid

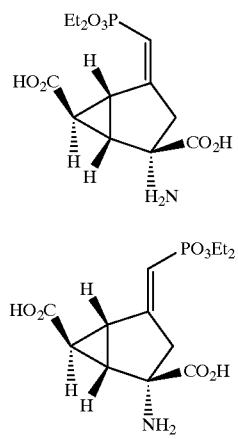

(a) (1S*,2S*,5R*,6S*)-Diethyl-2-(N-tert-butyloxycarbonyl)-amino-4-((E and Z)-diethylphoshonomethylene) Bicyclo-[3.1.0]hexane-2,6-dicarboxylate, Isomers A and B. The sodium salt of tetraethyl methylenediphosphonate was prepared by the addition of sodium bis(trimethylsilyl)amide (2.1 mmol) to an anhydrous toluene solution of tetraethyl methylenediphosphonate (0.6 g, 2.1 mmol) at 0° C. The sodium salt was rapidly added to a anhydrous toluene solution of the product of Example 5(a) (0.5 g, 1.4 mmol) at 0° C. and stirred for 15 minutes. The reaction was allowed to warm to room temperature and stir until it was determined to be complete by TLC. 1N HCl was added and the reaction mixture was extracted using ethyl acetate. The combined organic layers were washed with aqueous NaCl and dried with $MgSO_4$. The organics were concentrated and the crude product purified using HPLC (EtOAc/hexanes) to afford 0.190 g (28%) isomer A and 0.119 (17%) isomer B. Isomer A (E isomer): FDMS: M$_+$+1=490. Exact mass calcd. for $C_{22}H_{36}NO_9P$: 490.2206. Found: 490.2202Isomer B (Z isomer): FDMS: M$_+$+1=490.

(b) (1S*,2S*,5R*,6S*)-2-Amino-4-(Z)-diethylphosphonomethylenebicyclo[3.1.0]-hexane-2,6-dicarboxylic acid. The product of step (a), Isomer A (0.15 g, 0.31 mmol), was stirred in 2 mL of TFA for 1 hour, concentrated and dissolved in 5 mL of THF. The reaction was then treated with 2mL of 1N NaOH for 5 hours. The reaction mixture was concentrated and adjusted to pH=10 with 1N HCl. The resulting material was applied to an anion exchange resin (Bio-Rad® Ag1-X8), eluted with 1N HCl and recrystallized in $H_2O$ to afford 0.03 g (27%) of the desired product. FDMS: M++1= 334. Anal. calcd. for $C_{13}H_{20}NO_7P$÷2.6 eq. HCl: C, 36.48; H, 5.32; N, 3.27. Found: C, 36.33; H, 5.50; N, 3.72.

The other two title compounds are prepared in a similar manner, starting respectively from Isomer B or Isomer C.

EXAMPLE 18

(1S*,2S*,5R*,6S*)-2-Amino-4-Phosphonomethylene-bicyclo[3.1.0]hexane-2,6-Dicarboxylic acid

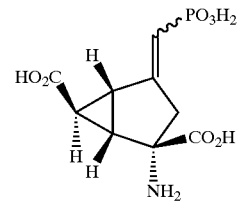

(a) (1S*,2S*,5R*,6S*)-2-Amino-4-phosphonomethylenebicyclo-[3.1.0]hexane-2,6-Dicarboxylic Acid. The product of Example 17(a), Isomer A (0;15 g, 0.31 mmol), was stirred in 2mL of TFA for 1 hour and concentrated. The resulting reaction material was treated with 6N HCl at reflux overnight, concentrated and resulting the product was triturated in $H_2$ O and IPA to afford 0.005 g (5%) of the desired product. FDMS: M$^+$+1=278.

EXAMPLE 19

(1S*,2S*,5R*,6S*)-2-Amino-4-Z-Cyanomethylenebicyclo-[3.1.0.]Hexane-2,6-Dicarboxylic Acid (1S*,2S*,5R*,6S*)-2-Amino-4-E-Cyanomethylenebicyclo-[3.1.0]Hexane-2,6-Dicarboxylic Acid

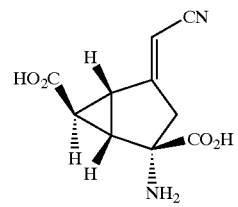

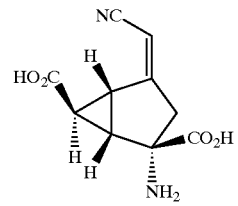

(a) (1S*,2S*,5R*,6S*)-Diethyl-2-(N-tert-butyloxycarbonyl)-amino-4-cyano-methylenebicyclo[3.1.0] hexane-2,6-dicarboxyate, Isomers A and B. The sodium salt of diethyl cyanomethylphosphonate was prepared by the addition of potassium bis (trimethyl-silyl) amide (2.6 mmol) to an anhydrous toluene solution of diethyl cyanomethylphosphonate (0.45 g, 2.6 mmol) at 0° C. The salt was rapidly added to the product of Example 5(a) (0.6 g, 1.7 mmol) at 0° C. and stirred for 15 minutes. The reaction was allowed to warm to room temperature and stir until it was determined to be complete by TLC. 1N HCl was added and the reaction mixture was extracted using ethyl acetate. The combined organic layers were washed with aqueous NaCl and dried with $MgSO_4$. The organics were concentrated and the crude product purified using HPLC (EtOAc/hexanes) to afford 0.525 g (82%) of a mixture of two isomers. Isomer A and Isomer B were separated using HPLC (EtOAc/Hexanes). Isomer A: $M^++1=379$. Exact mass calcd. for $C_{19}H_{26}N_2O_6$ (÷H) =379.1869. Found: 379.1875 Isomer B: $M^+=378$ (b) (1S*,2S*,5R*,6S*)-2-amino-4-cyanomethylenebicyclo-[3.1.0.]hexane-2,6-dicarboxylic acid. The product of step (a), Isomer A (0.15 g, 0.39 mmol), was stirred in 5 mL of TFA for 1 hour, concentrated and dissolved in 5 mL of THF. The reaction was then treated with 5 mL of 1N NaOH for 5 hours. The reaction was adjusted to a pH=7 with 1N HCl and concentrated to dryness. The resulting solid was reconstituted in water and the was adjusted to pH=10, applied to anion exchange resin (Bio-Rad® AG1–X8), eluted with 2N acetic acid, to afford 0.032 g (36%) of the desired product. FDMS: $M^++1=223$. Anal. calcd. for $C_{10}H_{10}N_2O_4$ +0.3 eq. $H_2O$: C, 52.77; H, 4.69; N, 12.31. Found: C, 52.53; H, 4.76; N, 12.17.

EXAMPLE 20

(1S*,2S*,4R*,5S*,6S*)-2-Aminobicyclo[3.1.0] Hexane-2,4,6-Tricarboxylic Acid

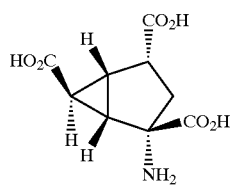

(a) (1S*,2S*,4R*,5S*,6S*)-Diethyl 2-(N-tert-butyloxycarbonyl)amino-4-cyanobicyclo-[3.1.0]hexane-2,6-dicarboxylate. To a solution of the product of Example 8(a) (1.45 g, 2.84 mmol) in dry dimethylsulfoxide (20 mL) was added sodium cyanide (700 mgs, 5 eq) and the reaction mixture stirred at 40° C. for 48 hours.

The reaction mixture was allowed to cool and then poured into water (200 mL). The aqueous phase was extracted with diethyl ether three times and the combined ethereal extracts washed with water and dried over magnesium sulfate. Filtration and evaporation in vacuo yielded a yellow foam (880 mg). This crude product was purified by chromatography on silica gel (eluant diethyl ether 25% hexane), to give the desired nitrile as a clear gum (670 mg).

$^1$H NMR (300 MHz, $CDCl_3$, δppm) : 1.30 (6H, t, $CO_2CH_2CH_1 \times 2$), 1.42 (9H, s, t-Butyl), 1.58 (1H, dd, $C_3$—H), 2.10 (1H, dd, $C_6$—H), 2.30 (2H, m, $C_1$—H ÷$C_5$—H), 3.05 (1H, dd, $C_3$—H), 3.55 (1H, m, $C_4$—H), 4.20 (4H, m, —$CO_2CH_2CH_3$=2), 5.40 (1H, s, NH).

(b) (1S*,2S*,4R*,5S*,6S*)-2-Aminobicyclo[3.1.0]hexane-2,4,6-tricarboxylic Acid. A mixture of the product of step (a) (64 mg, 0.175 mmol) and 2M hydrochloric acid (2 ml) was heated at 90° C. in a sealed vessel for 48 hours.

After cooling, the reaction mixture was evaporated in vacuo to give a white solid. (80 mg), which was dissolved in the minimum amount of water and purified by cation-exchange chromatography (Dowex 50×8–100; column eluted sequentially with $H_2O$, $H_2O$:THF 1:1 and $H_2O$ again. The amino acid was finally eluted with $H_2O$:pyridine 9:1). The pyridine was removed in vacuo and the residual solid redissolved in water and freeze-dried to give the desired amino acid as a fluffy white solid (38 mg) . Mpt. >300° C.

$^1$H NMR (300 MHz, $D_2O$, δppm) : 1.35 (1H, dd, $C_3$—H), 1.65 (1H, dd, $C_6$—H), 1.90 (1H, m, $C_5$—H), 2.00 (2H, m, $C_1$—H÷$C_3$—H), 3.18 (1H, m, $C_4$—H).

EXAMPLE 21

(1S*,2S*,4R*,5S*,6S*)-2-Amino-4-Cyanobicyclo [3.1.0]Hexane-2,6-Dicarboxylic Acid

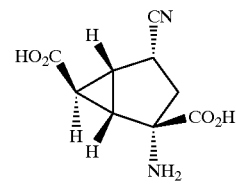

(a) (1S*,2S*,4R*,5S*,6S*)-2-(N-tert-butyloxycarbonyl) amino-4-cyanobicyclo[3.1.0]hexane-2,6-dicarboxylic acid. To a solution of the product of Example 20(a) (200 mg, 0.55 mmol) in tetrahydrofuran (2 ml) was added 1 molar lithium hydroxide solution (1.2 ml) and the mixture stirred at room temperature for 8 hours.

The reaction mixture was diluted with water, acidified with 1molar hydrochloric acid, and extracted three times with ethyl acetate. The combined organic extracts were washed with saturated sodium chloride solution, dried over magnesium sulfate, filtered and evaporated in vacuo to give a white glass (180 mg).

The crude produce was purified by chromatography on silica gel (eluant ethyl acetate 5% glacial acetic acid) to give the desired dicarboxylic acid as a white solid (120 mg). $^1$H NMR (300 MHz, DMSO-d6, δ ppm) : 1.38 (9H, s, t-butyl), 1.58 (1H, dd, $C_3$—H), 1.82 (1H, dd, $C_6$—H), 2.22 (1H, m, $C_5$—H), 2.36 (1H, m, $C_1$—H), 2.60 (1H, dd, $C_3$—H), 3.45 (1H, m, $C_4$—H), 7.30 (1H, s, NH).

(b) (1S*,2S*,4R*,5S*,6S*)-2-amino-4-cyanobicyclo [3.1.0]-hexane-2,6-dicarboxylic acid. The product of step (a) (120 mg. 0.38 mmol) was dissolved in trifluoroacetic acid (5 ml) and stirred at room temperature for 2 hours.

The reaction mixture was evaporated in vacuo, the residue redissolved in water and azeotroped in vacuo to give a white solid (62 mg). The crude solid was redissolved in the minimum of water and purified by cation-exchange chromatography (Dowex 50×8–100; column eluted sequentially with $H_2O$, $H_2O$:THF 1:1 and $H_2O$ again. The amino acid was finally eluted with $H_2O$:pyridine 9:1). The pyridine was removed in vacuo and the residual solid redissolved in water and freeze-dried to give the amino acid as a fluffy white solid (35 mg). Mpt. 240–242° C.

$^1$H NMR (300 MHz, $D_2O$, δ ppm) : 1.85 (1H, dd, $C_3$—H), 2.21 (1H, t, $C_6$—H), 2.42 (1H, dd, $C_1$—H), 2.60 (2H, m, $C_3$—H+$C_5$—H), 3.83 (1H, m, $C_4$—H).

EXAMPLE 22

(1S*,2S*,4R*,5S*,6S*)-2-Amino-4-Carboxamidobicyclo[3.1.0]hexane-2,6-Dicarboxylic Acid

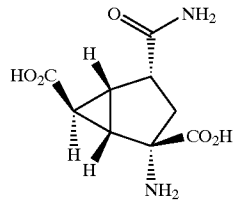

(a) (1S*,2S*,4R*,5S*,6S*)-2-(N-tert-butyloxycarbonyl)amino-4-carboxamidobicyclo[3.1.0]hexane-2,6-dicarboxylic acid. To a solution of the product of Example 20(a) (145 mg, 0.40 mmol) in absolute ethanol (1 ml) at 0–5° C. was added (1) 30% hydrogen peroxide (0.157 ml) (2) 6M sodium hydroxide (0.20 ml). The reaction mixture was allowed to warm to room temperature and stirred for a further 4 hours, when it was diluted with more water (4 ml).

After 72 hours the reaction mixture was acidified with 2M hydrochloric acid and extracted three times with ethyl acetate. The combined organic extracts were washed with saturated sodium chloride solution, dried over magnesium sulfate, filtered and evaporated in vacuo to give a white solid (84 mg). The crude product was purified by chromatography on silica gel (eluent ethyl acetate 5% glacial acetic acid) to give the desired acid as a white solid (34 mg).

$^1$H NMR (300 MHz, DMSO-d$_6$, δ ppm): 1.42 (9H, s, t-butyl), 1.65 (1H, dd, $C_3$—H), 1.75 (1H, broad s, $C_6$—H), 2.08 (2H, m, $C_1$—H+$C_3$—H), 2.14 (1H, m, $C_5$—H), 3.10 (1H, m, $C_4$—H), 6.90 (1H, s, NH), 7.44 (1H, s, NH), 7.64 (1H, s, NH), 12.35 (1H, broad hump, 2×CO$_2$H).

(b) (1S*,2S*,4R*,5S*,6S*)-2-Amino-4-carboxamidobicyclo-[3.1.0]hexane-2,6-dicarboxylic acid. A solution of the product of step (a) (34 mg, 0.1 mmol) in trifluoroacetic acid (5 ml) was stirred at room temperature for 2 hours.

The reaction mixture was then evaporated in vacuo to dryness, redissolved in water and then azeotroped in vacuo at 70° C. The crude solid was dissolved in the minimum volume of water and purified by cation-exchange chromatography (Dowex 50×8–100; column eluted sequentially with H$_2$O, H$_2$):THF 1:1 and H$_2$O again. The amino acid was finally eluted with H$_2$O:pyridine 9:1). The pyridine was removed in vacuo and the residual solid redissolved in water and freeze-dried to give the desired amino acid as a fluffy white solid (12 mg). Mpt. 260–262° C. (dec).

$^1$H NMR (300 MHz, D$_2$O, δ ppm): 1.95 (1H, dd, $C_3$—H), 2.30 (1H, d, $C_6$—H), 2.42–2.64 (3H, m, $C_2$—H+$C_3$—H+$C_5$—H), 3.78 (1H, m, $C_4$—H).

EXAMPLE 23

(1S*,2S*,4R*,5R*,6R*)-2-Amino-4-Hydroxybicyclo[3.1.0]Hexane-2,6-Dicarboxylic Acid

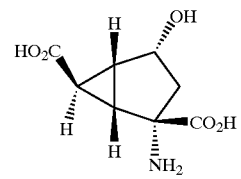

(a) (1S*,2S*,4R*,5R*,6R*)-Diethyl 2-N-t-butyloxycarbonylamino-4-hydroxybicyclo-[3.1.0]hexane-2,6-dicarboxylate. Potassium superoxide (0.52 g, 7.4 mmol) was added in one portion to a 0° C. solution of the product from Example 8a (1.90 g, 3.7 mmol) in anhydrous DMSO (20 mL). Upon complete addition the cooling bath was removed and the reaction mixture allowed to warm to ambient temperature as it stirred for 2 hours. The reaction mixture was diluted with EtOAc, washed with saturated aqueous Na$_2$S$_2$O$_3$, dried over MgSO$_4$ and concentrated under reduced pressure to yield the crude carbinol which was purified by PC-TLC (4 mm SiO$_2$ rotor-10% EtOAc/hexanes to 50% EtOAc/hexanes) to afford 0.29 g (22%, 0.81 mmol) of the desired product as a white foam. FDMS: M$^+$+1=258. Anal. calcd. for C$_{17}$H$_{27}$NO$_7$.0.75 H$_2$O: C, 55.05; H, 7.74; N, 3.78. Found: C, 55.39; H, 7.63; N, 3.38.

(b) A solution of the product from step (a) (0.24 g, 0.67 mmol), in EtOAc (30 mL) was chilled to 0° C. and purged with anhydrous HCl gas until the solution reached saturation. The cooling bath was removed and the reaction mixture stirred at ambient temperature for two hours, concentrated to dryness, and the resulting solid stirred in a 1:1 mixture of 1N NaOH:THF (20 mL total volume) at ambient temperature overnight. The reaction was adjusted to pH=7 with 1N HCl and concentrated under reduced pressure. The resulting solids were reconstituted in H$_2$O, adjusted to pH=12 with 1N NaOH, and purified by anion exchange chromatography (Bio-Rad® AG1–X8: acetate form converted to hydroxide form, elute with 3N acetic acid) to yield 0.12 g (0.58 mmol, 86%) of the desired product. mp=dec>270° C. FDMS: M$^+$+1=202. Anal. calcd. for C$_8$H$_{11}$NO$_5$: C, 47.76; H, 5.51; N, 6.96. Found: C, 47.51; H, 5.80; N, 6.72.

What is claimed is:

1. A compound of formula

III

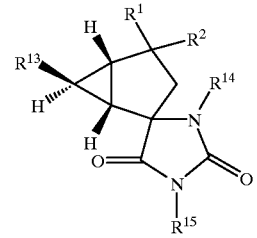

in which (a) R$^1$ represents fluoro, XOR$^3$, XNR$^4$R$^5$, SO$_3$H, tetrazol-5-yl, CN or PO$_3$R$_2^6$ and R$_2$ represents hydrogen; or
(b) R$^1$ and R$^2$ each represents fluoro; or
(c) R$^1$ and R$^2$ together represent =O, =NOR$^7$ or =CR$^8$R$^9$; or (d) one of $R^1$ and $R^2$ represents amino and the other represents carboxyl; or (e) $R^1$ represents $N_3$, $(CH_2)_mCOOR^{3a}$, $(CH_2)_mPO_3R^{6a}{}_2$, NHCONHR$^{3b}$ or NHSO$_2$R$^{3c}$ and $R^2$ represents hydrogen; or (f) $R^1$ and $R^2$ together represent =CHCOOR$^{3b}$, =CHPO$_3$R$_2{}^{6a}$ or =CHCN; and $R^3$ represents a hydrogen atom; a (1–6C) alkyl group; a (3–6C) alkenyl group; a (3–6C)alkynl group; an optionally substituted aromatic group; an optionally substituted heteroaromatic group; a non-aromatic carbocyclic group; a non-aromatic heteroarmatic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (3–6C) alkenyl or (3–6 C) alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups;

$R^{3a}$, $R^{3b}$ and $R^{3c}$ are as defined for $R^3$;

X represents a bond, CH$_2$ or CO;

m represents an integer of from 1 to 3;

$R^4$ represents COR$^{10}$ or is as defined for $R^3$;

$R^5$, $R^7$, $R^8$, $R^9$ and $R^{10}$ are as defined for $R^3$;

$R^6$ represents hydrogen or a (1–6 C)alkyl group;

$R^{6a}$ is defined for $R^6$;

$R^{13}$ represents a carboxyl group or an esterified carboxyl group, and $R^{14}$ and $R^{15}$ each independently represent a hydrogen atom, a (2–6 C) alkanoyl group, a (1–4 C) alkyl group, a (3–4 C) alkenyl group or a phenyl (1–4 C) alkyl group in which the phenyl is unsubstituted or substituted by halogen, (1–4 C) alkyl or (1–4 C) alkoxy, or a salt thereof.

2. A compound as claimed in claim 1, in which $R^{13}$ represents a (1–6 C) alkoxycarbonyl group.

3. A compound as claimed in claim 1, in which $R^{14}$ and $R^{15}$ are independently hydrogen or benzyl.

4. A compound as claimed in claim 1, in which $R^1$ represents fluoro, hydroxyl, PO$_3$H$_2$, methoxy, amino, azido, acetylamino, benzoylamino, methanesulfonylamino, methylaminocarbonylamino, N,N-dicyclopropylmethylamino, carboxy, cyano or carboxamido and $R^2$ represents hydrogen, or $R^1$ and $R^2$ together represent =O, =NOH or =CHCO$_2$H, =CH$_2$, =CHPO$_3$(C$_2$H$_5$)$_2$, =CHPO$_3$H$_2$ or =CHCN.

5. A compound as claimed in claim 4, in which $R^1$ represents hydroxyl and $R^2$ represents hydrogen.

6. A compound as claimed in claim 4, in which $R^1$ and $R^2$ together represent =O.

7. A compound as claimed in claim 1, in which $R^1$ represents hydroxyl and $R^2$ represents hydrogen, or $R^1$ and $R^2$ together represent =O;

$R^{13}$ represents a (1–6 C) alkoxycarbonyl group; and $R^{14}$ and $R^{15}$ are independently hydrogen or benzyl.

* * * * *

UNITED STATES PATENT AND TRADEMARK OFFICE
CERTIFICATE OF CORRECTION

PATENT NO. : 6,268,507 B1  
DATED : July 31, 2001  
INVENTOR(S) : Steven Marc Massey et al.

Page 1 of 1

It is certified that error appears in the above-identified patent and that said Letters Patent is hereby corrected as shown below:

<u>Column 39,</u>  
Line 12, delete the word "heteroarmatic" and replace with -- heterocyclic --.

Signed and Sealed this

Twenty-third Day of April, 2002

*Attest:*

*Attesting Officer*

JAMES E. ROGAN  
*Director of the United States Patent and Trademark Office*